United States Patent
Shen et al.

(10) Patent No.: US 11,234,421 B2
(45) Date of Patent: Feb. 1, 2022

(54) GENETICALLY MODIFIED NON-HUMAN ANIMAL WITH HUMAN OR CHIMERIC IL15

(71) Applicants: Biocytogen JiangSu Co., Ltd., Haimen (CN); Biocytogen Pharmaceuticals (Beijing) Co., Ltd., Beijing (CN)

(72) Inventors: Yuelei Shen, Beijing (CN); Meiling Zhang, Beijing (CN); Jiawei Yao, Beijing (CN); Chaoshe Guo, Beijing (CN); Yanan Guo, Beijing (CN); Yang Bai, Beijing (CN); Rui Huang, Beijing (CN); Lei Zhao, Beijing (CN)

(73) Assignees: Biocytogen JiangSu Co., Ltd., Jiangsu (CN); Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/012,696

(22) Filed: Sep. 4, 2020

(65) Prior Publication Data
US 2021/0051928 A1    Feb. 25, 2021

Related U.S. Application Data

(63) Continuation of application No. PCT/CN2019/128358, filed on Dec. 25, 2019.

(30) Foreign Application Priority Data

Dec. 25, 2018 (CN) .......................... 201811598044.3
Jun. 26, 2019 (CN) .......................... 201910560144.5

(51) Int. Cl.
| | | |
|---|---|---|
| A01K 67/027 | (2006.01) | |
| C12N 15/85 | (2006.01) | |
| A61K 49/00 | (2006.01) | |
| C07K 14/54 | (2006.01) | |

(52) U.S. Cl.
CPC ...... *A01K 67/0278* (2013.01); *A61K 49/0008* (2013.01); *C07K 14/5443* (2013.01); *C12N 15/8509* (2013.01); *A01K 2207/15* (2013.01); *A01K 2227/105* (2013.01); *A01K 2267/0325* (2013.01); *A01K 2267/0331* (2013.01); *C12N 2015/8563* (2013.01); *C12N 2015/8572* (2013.01); *C12N 2830/48* (2013.01)

(58) Field of Classification Search
CPC ............ A01K 67/0278; A01K 2207/15; A01K 2227/105; A01K 2267/0325; A01K 2267/0331; C07K 14/5443; A61K 49/0008; C12N 15/8509; C12N 2015/8563; C12N 2015/8572
USPC ................................................. 800/13, 18, 3
See application file for complete search history.

(56) References Cited

U.S. PATENT DOCUMENTS

| | | | |
|---|---|---|---|
| 4,683,195 A | 7/1987 | Mullis et al. | |
| 9,155,290 B2 * | 10/2015 | Rojas ................. | C12N 15/8509 |
| 2008/0063717 A1 | 3/2008 | Romagne et al. | |
| 2011/0231944 A1 | 9/2011 | Watarai et al. | |
| 2015/0106961 A1 | 4/2015 | Rojas et al. | |
| 2016/0295844 A1 * | 10/2016 | Herndler-Brandstetter ................. | A01K 67/0271 |
| 2019/0119701 A1 * | 4/2019 | Liang ........................ | C12N 9/22 |
| 2019/0320631 A1 | 10/2019 | Shen et al. | |

FOREIGN PATENT DOCUMENTS

| | | |
|---|---|---|
| CN | 102725400 | 10/2012 |
| CN | 105744829 | 7/2016 |
| CN | 107896479 | 4/2018 |
| CN | 108531487 | 9/2018 |
| JP | 2006-514024 | 4/2006 |
| WO | WO 2018001241 | 1/2018 |
| WO | WO 2018041118 | 3/2018 |
| WO | WO 2018041119 | 3/2018 |
| WO | WO 2018041120 | 3/2018 |
| WO | WO 2018041121 | 3/2018 |
| WO | WO 2018068756 | 4/2018 |
| WO | WO 2018086583 | 5/2018 |
| WO | WO 2018086594 | 5/2018 |
| WO | WO 2018113774 | 6/2018 |
| WO | WO 2018121787 | 7/2018 |
| WO | WO 2018177440 | 10/2018 |
| WO | WO 2018177441 | 10/2018 |

OTHER PUBLICATIONS

Coats et al. (2017) J. Visual. Exper., vol. 123, e55384: doi: 10.3791/55384, pp. 1-11.*
Yang et al. (1995) Development, vol. 121, 549-560.*
Auerbach et al., "Establishment and Chimera Analysis of 129/SvEv- and C57BL/6-Derived Mouse Embryonic Stem Cell Lines," BioTechniques, Nov. 2000, 29(5): 6 pages.
Brehm et al., "Generation of improved humanized mouse models for human infectious diseases," Journal of Immunological Methods, Aug. 2014, 410:3-17.
Festing et al., "Revised nomenclature for strain 129 mice," Mammalian Genome, Aug. 1999, 10: 836, 1 page.
GenBank Accession No. NC_000074.6, "Mus musculus strain C57BL/6J chromosome 8, GRCm38.p4 C57BL/6J," Jun. 22, 2016, 2 pages.
GenBank Accession No. NM_000585.4, "*Homo sapiens* interleukin 15 (IL15), transcript variant 3, mRNA," Dec. 6, 2017, 4 pages.
GenBank Accession No. NM_001254747.1, "Mus musculus interleukin 15 (Il15), transcript variant 2, mRNA," Dec. 18, 2017, 3 pages.
GenBank Accession No. NP_000576.1, "interleukin-15 isoform 1 preproprotein [*Homo sapiens*]," Dec. 6, 2017, 3 pages.
GenBank Accession No. NP_001241676.1, "interleukin-15 preproprotein [Mus musculus]," Dec. 18, 2017.

(Continued)

*Primary Examiner* — Anne Marie S Wehbe
(74) *Attorney, Agent, or Firm* — Fish & Richardson P.C.

(57) ABSTRACT

The present disclosure relates to genetically modified non-human animals that express a human or chimeric (e.g., humanized) IL15, and methods of use thereof.

22 Claims, 9 Drawing Sheets

Specification includes a Sequence Listing.

(56) References Cited

OTHER PUBLICATIONS

Ito et al., "NOD/SCID/ γcnull mouse: an excellent recipient mouse model for engraftment of human cells," Blood, Nov. 2002, 100(9): 3175-3182.
NCBI Gene ID 16168, "Il15 interleukin 15 [ *Mus musculus* (house mouse) ]," last updated Sep. 29, 2020, 11 pages.
NCBI Gene ID 25670, "Il15 interleukin 15 [ *Rattus norvegicus* (Norway rat) ]," last updated Jun. 9, 2020, 9 pages.
NCBI Gene ID 3600, "IL15 interleukin 15 [*Homo sapiens* (human) ]," last updated Aug. 23, 2020, 10 pages.
NCBI Gene ID 397683, "IL15 interleukin 15 [ *Sus scrofa* (pig) ]," last updated Jul. 21, 2020, 6 pages.
NCBI Gene ID 403584, "IL15 interleukin 15 [ *Canis lupus familiaris* (dog) ]," last updated Sep. 18, 2020, 4 pages.
NCBI Gene ID 699616, "IL15 interleukin 15 [*Macaca mulatta* (Rhesus monkey) ]," last updated Jun. 24, 2020, 4 pages.
PCT International Search Report and Written Opinion in International Appln. No. PCT/CN2019/128358, dated Mar. 27, 2020, 9 pages.
Pilipow et al. "IL15 and T-cell Stemness in T-cell-Based Cancer Immunotherapy," Cancer research, Dec. 2015, 75(24):5187-5193.
Rhode et al. "Comparison of the Superagonist Complex, ALT-803, to IL15 as Cancer Immunotherapeutics in Animal Models," Cancer Immunol. Res., Jan. 2016, 4(1):49-60.
Yao et al., "Tild-CRISPR allows for efficient and precise gene knockin in mouse and human cells," Developmental Cell, May 2018, 45:526-536.
Yin et al., "Delivery technologies for genome editing," Nature Reviews Drug Discovery, Jun. 2017, 16(6):387-399.
Zhu et al., "Humanising the mouse genome piece by piece," Nature communications, Apr. 23, 2019, 10(1):1-13.
Yang, "Aplastic anemia," Tianjin Science and Technology Translation Publishing Company, Nov. 2000, p. 119, English summary.

\* cited by examiner

FIG. 14

| Score | Expect | Method | Identities | Positives | Gaps |
|---|---|---|---|---|---|
| 223 bits(569) | 7e-81 | Compositional matrix adjust. | 118/162(73%) | 137/162(84%) | 0/162(0%) |

```
MOUSE    1   MKILKPYMRNTSISCYLCFLLNSHELTEAGIHVFILGCVSVGLPKTEANWIDVRYDLEKI    60
             M+I KP++R+ SI CY+C LLNSHFLTEAGIHVFILGC S GLPKTEANW++V  DL+KI
HUMAN    1   MRISKPHLRSISIQCYLCLLLNSHFLTEAGIHVFILGCFSAGLPKTEANWVNVISDLKKI    60

MOUSE   61   ESLIQSIHIDTTLYTDSDFHPSCKVTAMNCFLIELQVILHEYSNMTLNETVRNVLYLANS   120
             E LIQS+HID TLYT+SD HPSCKVTAM CFLLELQVI E  + ++++TV N++ LAN+
HUMAN   61   EDLIQSMHIDATLYTESDVHPSCKVTAMKCFLLELQVISLESGDASIHDTVENLLILANN   120

MOUSE  121   TLSSNKNVAESGCKECEELEEKTFTEEFLQSFTIRIVQMFINTS   162
             +LSSN NV ESGCKECEELEEK   EFLQSF+ IVQMFINTS
HUMAN  121   SLSSNGNVTESGCKECEELEEKNIKEFLQSFVHIVQMFINTS   162
```

GENETICALLY MODIFIED NON-HUMAN ANIMAL WITH HUMAN OR CHIMERIC IL15

CLAIM OF PRIORITY

This application is a bypass continuation of International Application PCT/CN2019/128358, with international filing date of Dec. 25, 2019, which claims the benefit of Chinese Patent Application App. No. 201811598044.3, filed on Dec. 25, 2018, Chinese Patent Application App. No. 201910560144.5, filed on Jun. 26, 2019. The entire contents of the foregoing are incorporated herein by reference.

TECHNICAL FIELD

This disclosure relates to genetically modified animal expressing human or chimeric (e.g., humanized) IL15, and methods of use thereof.

BACKGROUND

Immunodeficient animals are very important for disease modeling and drug developments. In recent years, immunodeficient mice are routinely used as model organisms for research of the immune system, cell transplantation strategies, and the effects of disease on mammalian systems. They have also been extensively used as hosts for normal and malignant tissue transplants, and are widely used to test the safety and efficacy of therapeutic agents.

However, the engraftment capacity of these immunodeficient animals can vary. More immunodeficient animals with different genetic makeup and better engraftment capacities are needed.

SUMMARY

This disclosure is related to an animal model with human IL15 or chimeric IL15. The animal model can express human IL15 or chimeric IL15 (e.g., humanized IL15) protein in its body. It can be used in the studies on the function of IL15 gene, and can be used in the screening and evaluation of anti-human IL15 antibodies. In addition, the animal models prepared by the methods described herein can be used in drug screening, pharmacodynamics studies, treatments for immune-related diseases (e.g., autoimmune disease), and cancer therapy. Furthermore, the animal has an enhanced engraftment capacity of exogenous cells (e.g., relative to a NOD/scid animal or is a NOD-Prkdc$^{scid}$IL-2rg$^{null}$ animal).

In one aspect, the disclosure is related to a genetically-modified, non-human animal whose genome comprises at least one chromosome comprising a sequence encoding a human or chimeric IL15.

In some embodiments, the sequence encoding a human or chimeric IL15 comprises a sequence encoding an amino acid sequence that is at least 70%, 75%, 80%, 85%, 90%, 95%, 99%, or 100% identical to human IL15 (NP_000576.1 (SEQ ID NO: 4)).

In some embodiments, the sequence encoding a human or chimeric IL15 is operably linked to a Woodchuck Hepatitis Virus (WHP) Posttranscriptional Regulatory Element and/or a polyA (polyadenylation) signal sequence.

In some embodiments, the sequence encoding the human or chimeric IL15 is operably linked to an endogenous regulatory element at the endogenous IL15 gene locus in the at least one chromosome.

In some embodiments, the sequence encoding a human or chimeric IL15 is operably linked to an endogenous 5'-UTR.

In some embodiments, the animal is a mammal, e.g., a monkey, a rodent, a rat, or a mouse.

In some embodiments, the animal in its genome comprises a sequence that is a least 70%, 75%, 80%, 85%, 90%, 95%, 99%, or 100% identical to SEQ ID NO: 5, SEQ ID NO: 6, SEQ ID NO: 9, or SEQ ID NO:51.

In some embodiments, the animal does not express endogenous IL15, or expresses a decreased level of endogenous IL15.

In some embodiments, the animal has one or more cells expressing human or chimeric IL15.

In one aspect, the disclosure is related to a genetically-modified, non-human animal.

In some embodiments, the genome of the animal comprises an insertion of a sequence encoding a human IL15 or a chimeric IL15 at an endogenous IL15 gene locus.

In some embodiments, the sequence encoding the human IL15 or the chimeric IL15 is operably linked to the 5'-UTR at the endogenous IL15 locus.

In some embodiments, the sequence encoding the human IL15 or the chimeric IL15 is inserted before IL15 endogenous start codon (e.g., immediately before start codon).

In some embodiments, the animal does not express endogenous IL15, and one or more cells of the animal expresses the human IL15 or the chimeric IL15.

In some embodiments, the animal is a mouse, and the sequence encoding the chimeric IL15 comprises one or more exons selected from the group consisting of exon 1, exon 2, exon 3, exon 4, exon 5, exon 6, exon 7, and exon 8 of human IL15 gene.

In some embodiments, the animal is heterozygous with respect to the insertion at the endogenous IL15 gene locus.

In some embodiments, the animal is homozygous with respect to the insertion at the endogenous IL15 gene locus.

In one aspect, the disclosure is related to a method for making a genetically-modified, non-human animal, comprising: inserting in at least one cell of the animal, at an endogenous IL15 gene locus, a sequence encoding an exogenous IL15.

In some embodiments, the endogenous IL15 gene locus is located at exon 1, exon 2, exon 3, exon 4, exon 5, exon 6, exon 7, or exon 8.

In some embodiments, the exogenous IL15 has a sequence that is at least 50%, 60%, 70%, 80%, 90% or 100% identical to SEQ ID NO: 4.

In some embodiments, the animal is a mouse, and the sequence encoding the exogenous IL15 is inserted before IL15 endogenous start codon (e.g., immediately before start codon).

In one aspect, the disclosure is related to a non-human animal comprising at least one cell comprising a nucleotide sequence encoding an exogenous IL15 polypeptide, In some embodiments, the exogenous IL15 polypeptide comprises at least 50 contiguous amino acid residues that are identical to the corresponding contiguous amino acid sequence of a human IL15.

In some embodiments, the exogenous IL15 polypeptide comprises a sequence that is at least 80%, 90%, 95%, or 99% identical to SEQ ID NO: 4.

In some embodiments, the nucleotide sequence is operably linked to the 5'-UTR at the endogenous IL15 locus.

In some embodiments, the nucleotide sequence is integrated to an endogenous IL15 gene locus of the animal.

In some embodiments, the animal in its genome comprises from 5' to 3' mouse exon 1, mouse intron 1, mouse exon 2, mouse intron 2, a part of mouse exon 3, a sequence encoding the exogenous IL15 polypeptide, a part of mouse exon 3, mouse intron 3, mouse exon 4, mouse intron 4, mouse exon 5, mouse intron 5, mouse exon 6, mouse intron 6, mouse exon 7, mouse intron 7, and mouse exon 8.

In some embodiments, the sequence encoding the exogenous IL15 polypeptide further comprises a Woodchuck Hepatitis Virus (WHP) Posttranscriptional Regulatory Element, and/or a polyA (polyadenylation) signal sequence.

In some embodiments, the animal is a NOD-Prkdc$^{scid}$IL-2rg$^{null}$ mouse.

In some embodiments, the animal further comprises a sequence encoding an additional human or chimeric protein.

In some embodiments, the additional human or chimeric protein is programmed cell death protein 1 (PD-1), cytotoxic T-lymphocyte-associated protein 4 (CTLA-4), Lymphocyte Activating 3 (LAG-3), IL15 receptor, B And T Lymphocyte Associated (BTLA), Programmed Cell Death 1 Ligand 1 (PD-L1), CD3, CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα) or TNF Receptor Superfamily Member 4 (OX40).

In some embodiments, the animal is a NOD-Prkdc$^{scid}$IL-2rg$^{null}$ mouse.

In some embodiments, the animal or mouse further comprises a sequence encoding an additional human or chimeric protein.

In some embodiments, the additional human or chimeric protein is PD-1, CTLA-4, LAG-3, IL15 receptor, BTLA, PD-L1, CD3, CD27, CD28, CD47, CD137, CD154, TIGIT, TIM-3, GITR, SIRPα or OX40.

In one aspect, the disclosure is related to a method of determining effectiveness of an anti-IL15 antibody in treating an immune disorder, comprising: administering the anti-IL15 antibody to the animal as described herein; and determining the effects of the anti-IL15 antibody in treating the immune disorder.

In some embodiments, the immune disorder is an allergy or an auto-immune disease (e.g., rheumatoid arthritis).

In one aspect, the disclosure is related to a method of determining effectiveness of an IL15 pathway modulator in modulating IL15 pathway activity, comprising: administering the IL15 modulator to the animal as described herein; and determining the effects of the IL15 modulator in IL15 pathway activity.

In some embodiments, the animal comprises one or more cells that express IL15 receptor (e.g., human IL15 receptor).

In some embodiments, the IL15 pathway modulator is an anti-IL15 antibody or an anti-IL15R antibody.

In one aspect, the disclosure is related to a method of determining effectiveness of an agent or a combination of agents for the treatment of cancer, comprising: engrafting tumor cells to the animal as described herein, thereby forming one or more tumors in the animal; administering the agent or the combination of agents to the animal; and determining the inhibitory effects on the tumors.

In some embodiments, before engrafting the tumor cells to the animal, human peripheral blood cells (hPBMC) or human hematopoietic stem cells are injected to the animal.

In some embodiments, the tumor cells are from cancer cell lines.

In some embodiments, the tumor cells are from a tumor sample obtained from a human patient.

In some embodiments, the inhibitory effects are determined by measuring the tumor volume in the animal.

In some embodiments, the tumor cells are melanoma cells, lung cancer cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

In some embodiments, the agent is IL15.

In some embodiments, the agent is an anti-PD-1 antibody.

In some embodiments, the combination of agents comprises one or more agents selected from the group consisting of paclitaxel, cisplatin, carboplatin, pemetrexed, 5-FU, gemcitabine, oxaliplatin, docetaxel, and capecitabine.

In one aspect, the disclosure is related to a method of producing an animal comprising a human hemato-lymphoid system, the method comprising: engrafting a population of cells comprising human hematopoietic cells or human peripheral blood cells into the animal as described herein.

In some embodiments, the human hemato-lymphoid system comprises human cells selected from the group consisting of hematopoietic stem cells, myeloid precursor cells, myeloid cells, dendritic cells, monocytes, granulocytes, neutrophils, mast cells, lymphocytes, and platelets.

In some embodiments, provide herein is a method of producing an animal comprising a human hemato-lymphoid system that further comprising: irradiating the animal prior to the engrafting.

In one aspect, the disclosure is related to a genetically-modified, non-human animal, In some embodiments, the genome of the animal comprises a replacement of a sequence encoding endogenous IL 15 with a corresponding sequence encoding a human IL15 at an endogenous IL15 gene locus.

In some embodiments, the sequence encoding the human IL15 or the chimeric IL15 is operably linked to the 5'-UTR at the endogenous IL15 locus, and one or more cells of the animal expresses the human IL15 or the chimeric IL15.

In some embodiments, the animal does not express endogenous IL15.

In some embodiments, the animal is a mouse, and the sequence encoding the chimeric IL15 comprises one or more exons selected from the group consisting of exon 1, exon 2, exon 3, exon 4, exon 5, exon 6, exon 7, and exon 8 of human IL15 gene.

In some embodiments, the animal is heterozygous with respect to the replacement at the endogenous IL15 gene locus.

In some embodiments, the animal is homozygous with respect to the replacement at the endogenous IL15 gene locus.

In one aspect, the disclosure is related to a method for making a genetically-modified, non-human animal, comprising: replacing in at least one cell of the animal, at an endogenous IL15 gene locus, a sequence encoding a region of an endogenous IL15 with a sequence encoding a corresponding region of human IL15.

In some embodiments, the sequence encoding the corresponding region of human IL15 comprises exon 1, exon 2, exon 3, exon 4, exon 5, exon 6, exon 7, and/or exon 8, or a part thereof, of a human IL15 gene.

In some embodiments, the sequence encoding the corresponding region of human IL15 encodes a sequence that is at least 50%, 60%, 70%, 80%, or 90% identical to SEQ ID NO: 4.

In some embodiments, the animal is a mouse, and the endogenous IL15 locus is exon 1, exon 2, exon 3, exon 4, exon 5, exon 6, exon 7, and/or exon 8 of the mouse IL15 gene.

In one aspect, the disclosure is related to a method of making a genetically-modified mouse cell that expresses a chimeric IL15, the method comprising: replacing at an endogenous mouse IL15 gene locus, a nucleotide sequence encoding a region of mouse IL15 with a nucleotide sequence encoding a corresponding region of human IL15, thereby generating a genetically-modified mouse cell that includes a nucleotide sequence that encodes the chimeric IL15, In some embodiments, the mouse cell expresses the chimeric IL15.

In some embodiments, the nucleotide sequence encoding the chimeric IL15 is operably linked to an endogenous promoter and/or a Woodchuck Hepatitis Virus (WHP) Post-transcriptional Regulatory Element, and/or a polyA (polyadenylation) signal sequence.

In one aspect, the disclosure is related to a method of determining effectiveness of an anti-IL15 antibody for the treatment of cancer, comprising: administering the anti-IL15 antibody to the animal as described herein, wherein the animal has a tumor; and determining the inhibitory effects of the anti-IL15 antibody to the tumor.

In some embodiments, the tumor comprises one or more cells that express IL15.

In some embodiments, the tumor comprises one or more cancer cells that are injected into the animal.

In some embodiments, determining the inhibitory effects of the anti-IL15 antibody to the tumor involves measuring the tumor volume in the animal.

In some embodiments, the tumor cells are solid tumor cells.

In one aspect, the disclosure is related to a method of determining effectiveness of an anti-IL15 antibody and an additional therapeutic agent for the treatment of a tumor, comprising administering the anti-IL15 antibody and the additional therapeutic agent to the animal as described herein, wherein the animal has a tumor; and determining the inhibitory effects on the tumor.

In some embodiments, the animal further comprises a sequence encoding a human or chimeric programmed cell death protein 1 (PD-1).

In some embodiments, the animal further comprises a sequence encoding a human or chimeric cytotoxic T-lymphocyte antigen 4 (CTLA4).

In some embodiments, the additional therapeutic agent is an anti-PD-1 antibody or an anti-CTLA4 antibody.

In some embodiments, the tumor comprises one or more tumor cells that express IL15, PD-L1 or PD-L2.

In some embodiments, the tumor is caused by injection of one or more cancer cells into the animal.

In some embodiments, determining the inhibitory effects of the treatment involves measuring the tumor volume in the animal.

In some embodiments, the animal has solid tumors, glioma, head and neck cancer, melanoma, thyroid cancer, breast cancer, pancreatic cancer, colon cancer, bladder cancer, ovarian cancer, prostate cancer, or leukemia.

In one aspect, the disclosure is related to a nucleic acid comprising a nucleotide sequence, in some embodiments, the nucleotide sequence is one of the following: (a)

a sequence that encodes the protein as described herein;
(b) SEQ ID NO: 5, 6, or 9; (c) a sequence that is at least 90% identical to SEQ ID NO: 5, 6, or 9; and (d) a sequence that is at least 91%, 92%, 93%, 94%, 95%, 96%, 97%, 98%, or 99% identical to SEQ ID NO: 5, 6, or 9.

In one aspect, the disclosure is related to a cell comprising the nucleic acid as described herein.

In one aspect, the disclosure is related to an animal comprising the nucleic acid as described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 14 shows the alignment between mouse IL15 amino acid sequence (NP_001241676.1; SEQ ID NO: 2) and human IL15 amino acid sequence (NP_000576.1; SEQ ID NO: 4).

SEQUENCE LISTING

Figure 1:
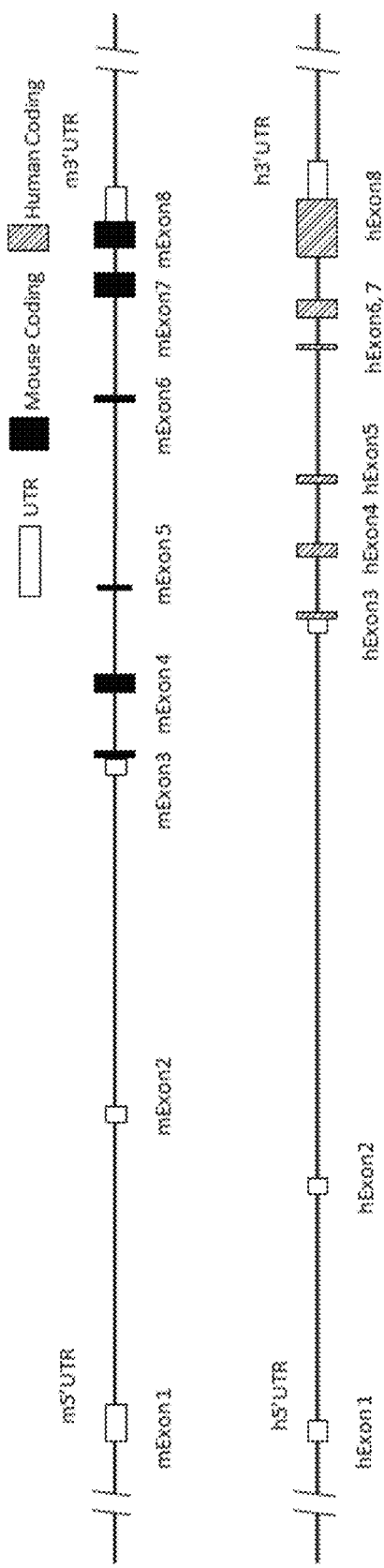
FIG. 1 is a schematic diagram showing the mouse IL15 gene locus and human IL15 gene locus.

The instant application contains a Sequence Listing which has been submitted electronically in ASCII format its hereby incorporated by reference in its entirety. Said ASCII copy, created on Nov. 3, 2020, is named UPDATED_SEQ.txt and is 32, 581 bytes in size.

DETAILED DESCRIPTION

This disclosure relates to transgenic non-human animal with human or chimeric (e.g., humanized) IL15, and methods of use thereof.

Signaling pathway of IL-15 begins with binding to IL-15Rα receptor, with subsequent presentation to surrounding cells bearing IL-15βγc complex on their cell surface. Upon binding IL-150 subunit activates Janus kinase 1 (Jak1) and γc subunit Janus kinase 3 (Jak3), which leads to phosphorylation and activation of signal transducer and activator of transcription 3 (STAT3) and STAT5. Due to sharing of receptor subunits between IL-2 and IL-15, both of these cytokines have similar downstream effects including the induction of B-cell lymphoma (Bcl-2), MAP (mitogen-activated protein kinase) kinase pathway and the phosphorylation of Lck (lymphocyte-activated protein tyrosine kinase) and Syk (spleen tyrosine kinase) kinases, which leads to cell proliferation and maturation.

In mast cells, the IL-15R signaling pathway has been found to include Jak2 and STAT5 instead Jak1/3 and STAT3/5. Phosphorylation STATs form transcription factors and activate transcription of appropriate genes. The β chain of IL-15R recruits and also activates protein tyrosine kinases of the Src family including Lck, Fyn and Lyn kinase. It also activates phosphatidylinositol 3-kinase (PI3K) and AKT signaling pathway and induce expression of transcription factors including c-Fos, c-Jun, c-Myc and NF-κB.

IL-15 is also able to bind to the 15Rβγc signaling complex with intermediate affinity without requirement for IL-15Ra receptor. Upon binding IL-15 to signaling complex, kinases of the Src family including Lck and Fyn are activated, and subsequently activates PI3K and MAPK signaling pathway. The second mechanism of IL-15 action is cis-presentation, when IL-15 is presented by IL-15Ra to 15Rβγc signaling complex on the same cell. This mechanism is mediated by the C-terminus flexibility which is mediated by 32 amino acids linker and/or 74 amino acids long PT region.

IL-15 regulates the activation and proliferation of T and natural killer (NK) cells. Survival signals that maintain memory T cells in the absence of antigen are provided by IL-15. This cytokine is also implicated in NK cell development. In rodent lymphocytes, IL-15 prevents apoptosis by inducing BCL2L1/BCL-x(L), an inhibitor of the apoptosis pathway. In humans with celiac disease IL-15 similarly suppresses apoptosis in T-lymphocytes by inducing Bcl-2 and/or Bcl-xL. A hematopoietin receptor, the IL-15 receptor that binds IL-15 propagates its function. Some subunits of the IL-15 receptor are shared in common with the receptor for a structurally related cytokine called Interleukin 2 (IL-2) allowing both cytokines to compete for and negatively regulate each other's activity. CD8+ memory T cell number is controlled by a balance between IL-15 and IL-2. When IL-15 binds its receptor, JAK kinase, STAT3, STAT5, and STATE transcription factors are activated to elicit downstream signaling events. Thus, IL15 antibodies can be potentially used as cancer therapies.

Experimental animal models are an indispensable research tool for studying the effects of these antibodies (e.g., IL15 antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels. In addition, because human IL15 can have better interactions with cells in a human hemato-lymphoid system, the animal has a much higher success rate to construct a human hemato-lymphoid system (e.g., by engrafting a population of cells comprising human hematopoietic cells or human peripheral blood cells into the animal).

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N. Y., 1986); each of which is incorporated herein by reference in its entirety.

Interleukin-15

Interleukin-15 (IL-15 or IL15) is 14-15 kDa glycoprotein encoded by the 34 kb region of chromosome 4q31 in humans, and at the central region of chromosome 8 in mice. Although IL-15 mRNA can be found in many cells and tissues including mast cells, cancer cells or fibroblasts, this cytokine is produced as a mature protein mainly by dendritic cells, monocytes and macrophages.

IL15 is a 4-a-helix bundle cytokine playing a pivotal role in stimulation of both innate and adaptive immune cells. IL15 induces the activation, the proliferation, and the survival of T cells and contributes to generation and maintenance of high-avidity, antigen-specific CD8+ memory T cells in the long term. In addition, IL15 is involved in the development, the persistence, and the activation of NK and NKT as well as γ/δ T cells The IL15 receptor (IL15R) is composed of three different molecules, better known as the α (CD215; unique to the IL15R), the β (CD122), and the γ (CD132) chains. In particular, CD122 is also a component of the IL2R, whereas CD132, also known as the common γ chain ($γ_c$), is shared with different cytokines, including IL2, IL4, IL7, IL9, and IL21. While the IL15Rβγ complex is present on target cells, IL15Rα can be expressed as a membrane-bound complex with IL15 on the surface of many cell types, including activated monocytes, dendritic cells (DC), and endothelial cells. Such a heterodimer is presented in trans to neighboring α/β, γ/δ T or NK cells. Alternatively, it can be shed and released as a soluble factor. It was indicated that virtually all circulating IL15 in human and mouse serum is complexed with IL15Ra. Triggering of the receptor activates downstream signaling pathways that include JAK1 and JAK3 as well as STAT3 and STAT5, followed by the recruitment of the PI3K/AKT/mTOR and RAS/RAF/MAPK-ERK cascades. By inducing FOS/JUN, MYC, NF-κB, and BCL2 genes expression and by decreasing the expression of BIM and PUMA, IL15 has a stimulating effect on T-cell proliferation and survival.

Because sharing the β and γ components of the receptor, IL2 and IL15 exert similar functions on T cells. Indeed, both stimulate the proliferation of T cells, facilitate the differentiation of cytotoxic T lymphocytes (CTL), and induce the generation and maintenance of NK cells. Nevertheless, mice deficient in IL2 or IL15 have different phenotypes, and administration of IL2 and IL15 to mice, primates, or humans leads to distinct effects on cells of the immune system. As regards to antigen-activated effector cells, while IL2 promotes terminal differentiation and, eventually, their elimination by activation-induced cell death (AICD), IL15 inhibits AICD and promotes the generation of long-lived memory T cells as well as their maintenance by homeostatic proliferation.

IL15 and its IL15Rα chain are coexpressed by monocytes/macrophages and dendritic cells and subsequently displayed as a cell surface IL15:IL15Rα complex, which is trans-presented to neighboring immune cells expressing IL2Rβγc. Therefore, IL15 does not support maintenance of Tregs. Rather than inducing apoptosis of activated CD8+ T cells, IL15 provides anti-apoptotic signals. IL15 also has non-redundant roles in the development, proliferation, and activation of NK cells. IL15 does not induce significant capillary leak syndrome in mice or nonhuman primates (NHP), suggesting that IL15-based therapies may provide the immunostimulatory benefits of IL2 with fewer adverse effects.

A detailed description of IL15 and its function can be found, e.g., in Pilipow, et al. "IL15 and T-cell Stemness in T-cell-Based Cancer Immunotherapy." Cancer research 75.24 (2015): 5187-5193; Rhode, et al. "Comparison of the superagonist complex, ALT-803, to IL15 as cancer immunotherapeutics in animal models." Cancer immunology research 4.1 (2016): 49-60; each of which is incorporated by reference in its entirety.

In human genomes, IL15 gene (Gene ID: 3600) locus has eight exons, exon 1, exon 2, exon 3, exon 4, exon 5, exon 6, exon 7, and exon 8 (FIG. 1). The nucleotide sequence for human IL15 mRNA is NM_000585.4 (SEQ ID NO: 3), and the amino acid sequence for human IL15 is NP_000576.1 (SEQ ID NO: 4). The location for each exon and each region in human IL15 nucleotide sequence and amino acid sequence is listed below:

TABLE 1

| human IL15 (approximate location) | NM_000585.4 2012bp (SEQ ID NO: 3) | NP_000576.1 162aa (SEQ ID NO: 4) |
| --- | --- | --- |
| Exon 1 | 1-153 | non-coding |
| Exon 2 | 154-275 | non-coding |
| Exon 3 | 276-386 | 1-4 |
| Exon 4 | 387-484 | 5-37 |
| Exon 5 | 485-569 | 38-65 |
| Exon6 | 570-614 | 66-80 |
| Exon 7 | 615-752 | 81-126 |
| Exon 8 | 753-2002 | 127-162 |
| Signal peptide | 375-461 | 1-29 |
| Donor region in Example | 375-863 | 1-162 |

In mice, IL15 gene locus has eight exons, exon 1, exon 2, exon 3, exon 4, exon 5, exon 6, exon 7, and exon 8 (FIG. 1). The nucleotide sequence for mouse IL15 mRNA is NM_001254747.1 (SEQ ID NO: 1), the amino acid sequence for mouse IL15 is NP_001241676.1 (SEQ ID NO: 2). The location for each exon and each region in the mouse IL15 nucleotide sequence and amino acid sequence is listed below:

TABLE 2

| Mouse IL15 (approximate location) | NM_001254747.1 1287 bp (SEQ ID NO: 1) | NP_001241676.1 162aa (SEQ ID NO: 2) |
| --- | --- | --- |
| Exon 1 | 1-287 | non-coding |
| Exon 2 | 288-409 | non-coding |
| Exon 3 | 410-508 | 1-4 |
| Exon 4 | 509-606 | 5-37 |
| Exon 5 | 607-691 | 38-65 |
| Exon6 | 692-736 | 66-80 |
| Exon 7 | 737-874 | 81-126 |
| Exon 8 | 875-1275 | 127-162 |
| Signal peptide | 497-583 | 1-29 |
| Replaced region in Example | NA | NA |

The mouse IL15 gene (Gene ID: 16168) is located in Chromosome 8 of the mouse genome, which is located from 82331624 to 82403272, of NC_000074.6 (GRCm38.p4 (GCF_000001635.24)). The 5'-UTR is from 82,402,570 to 82,402,300, and 82,379,615 to 82,379,494, and 82,345,698 to 82,345,612, exon 1 is from 82,402,570 to 82,402,300, the first intron is from 82,402,299 to 82,379,616, exon 2 is from 82,379,615 to 82,379,494, the second intron is from 82,379, 493 to 82,345,699, exon 3 is from 82,345,698 to 82,345,600, the third intron is from 82,345,599 to 82,344,473, exon 4 is from 82,344,472 to 82,344,375, the fourth intron is from 82,344,374 to 82,343,324, exon 5 is from 82,343,323 to 82,343,239, the fifth intron is from 82,343,238 to 82,337, 611, exon 6 is from 82,337,610 to 82,337,566, the sixth intron is from 82,337,565 to 82,334,607, exon 7 is from 82,334,606 to 82,334,469, the seventh intron is from 82,334, 468 to 82,332,025, exon 8 is from 82,332,024 to 82,331,632, the 3'-UTR is from 82,331,913 to 82,331,632, based on transcript NM_001254747.1. All relevant information for mouse IL15 locus can be found in the NCBI website with Gene ID: 16168, which is incorporated by reference herein in its entirety.

FIG. 14 shows the alignment between mouse IL15 amino acid sequence (NP_001241676.1; SEQ ID NO: 2) and human IL15 amino acid sequence (NP_000576.1; SEQ ID NO: 4). Thus, the corresponding amino acid residue or region between human and mouse IL15 can be found in FIG. 14.

IL15 genes, proteins, and locus of the other species are also known in the art. For example, the gene ID for IL15 in *Rattus norvegicus* is 25670, the gene ID for IL15 in *Macaca mulatta* (Rhesus monkey) is 699616, the gene ID for IL15 in *Canis lupus familiaris* (dog) is 403584, and the gene ID for IL15 in *Sus scrofa* (pig) is 397683. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) IL15 nucleotide sequence and/or amino acid sequences.

In some embodiments, the human or chimeric IL15 has an amino acid sequence that is at least 70%, 75%, 80%, 85%, 90%, 95%, 99%, or 100% identical to human IL15 (NP_000576.1 (SEQ ID NO: 4)).

In some embodiments, the sequence encoding a human or chimeric IL15 is operably linked to a Woodchuck Hepatitis Virus (WHP) Posttranscriptional Regulatory Element and/or a polyA (polyadenylation) signal sequence. In some embodiments, the sequence is operably linked to an endogenous regulatory element at the endogenous IL15 gene locus in the at least one chromosome.

In some embodiments, the sequence encoding a human IL15 or a chimeric IL15 is inserted at an endogenous IL15 gene locus (e.g., exon 1, exon 2, exon 3, exon 4, exon 5, exon 6, exon 7, and exon 8 of endogenous IL15 gene locus). In some embodiments, the sequence is inserted before IL15 endogenous start codon (e.g., immediately before start codon).

In some embodiments, a region or a portion of endogenous IL15 sequences (e.g., nucleic acid sequences or amino acid sequences) are replaced by the corresponding human sequences. In some embodiments, the entire sequence of mouse exon 1, exon 2, exon 3, exon 4, exon 5, exon 6, exon 7, exon 8, and signal peptide, are replaced by the corresponding human sequence. In some embodiments, a "region" or "portion" of mouse exon 1, exon 2, exon 3, exon 4, exon 5, exon 6, exon 7, exon 8, and/or signal peptide are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, or signal peptide. In some embodiments, a region, a portion, or the entire sequence of mouse exon 1, exon 2, exon 3, exon 4, exon 5, exon 6, exon 7, and/or exon 8 (e.g., exon 1, exon 2, exon 3, exon 4, exon 5, exon 6, exon 7 and exon 8) are replaced by the human exon 1, exon 2, exon 3, exon 4, exon 5, exon 6, exon 7, and/or exon 8 (e.g., exon1, exon 2, exon 3, exon 4, exon 5, exon 6, exon 7 and exon 8) sequence.

In some embodiments, the present disclosure also provides a chimeric (e.g., humanized) IL15 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse IL15 mRNA sequence (e.g., SEQ ID NO: 1), mouse IL15 amino acid sequence (e.g., SEQ ID NO: 2), or a portion thereof (e.g., exon 1, exon 2, exon 3, exon 4, exon 5, exon 6, exon 7 and exon 8); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human IL15 mRNA sequence (e.g., SEQ ID NO: 3), human IL15 amino acid sequence (e.g., SEQ ID NO: 4), or a portion thereof (e.g., exon 1, exon 2, exon 3, exon 4, exon 5, exon 6, exon 7 and exon 8).

In some embodiments, the sequence encoding full-length mouse IL15 protein (SEQ ID NO: 2) is replaced. In some embodiments, the sequence is replaced by a sequence encoding a corresponding region of human IL15 (e.g., full-length of human IL15 protein (SEQ ID NO: 4)).

In some embodiments, the nucleic acids as described herein are operably linked to a promotor or regulatory element, e.g., an endogenous mouse IL15 promotor, an inducible promoter, an enhancer, and/or mouse or human regulatory elements.

In some embodiments, the nucleic acids as described herein are operably linked to a Woodchuck Hepatitis Virus (WHP) Posttranscriptional Regulatory Element (WPRE) and/or a polyA (polyadenylation) signal sequence. The WPRE element is a DNA sequence that, when transcribed, creates a tertiary structure enhancing expression. The sequence can be used to increase expression of genes delivered by viral vectors. WPRE is a tripartite regulatory element with gamma, alpha, and beta components. The full tripartite WPRE sequence is set forth in nucleic acids 914-1502 of SEQ ID NO: 9. In some embodiments, the WPRE sequence has a sequence that is at least 70%, 80%, 90%, or 95% identical to nucleic acids 914-1502 of SEQ ID NO: 9.

In some embodiments, the polyA (polyadenylation) signal sequence has a sequence that is at least 70%, 80%, 90%, or 95% identical to nucleic acids 1523-1730 of SEQ ID NO: 9.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides)

that are different from a portion of or the entire mouse IL15 nucleotide sequence (e.g., exon 1, exon 2, exon 3, exon 4, exon 5, exon 6, exon 7, exon 8, or NM_001254747.1 (SEQ ID NO: 1)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse IL15 nucleotide sequence (e.g., exon 1, exon 2, exon 3, exon 4, exon 5, exon 6, exon 7, exon 8, or NM_001254747.1 (SEQ ID NO: 1)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human IL15 nucleotide sequence (e.g., exon 1, exon 2, exon 3, exon 4, exon 5, exon 6, exon 7, exon 8, or NM_000585.4 (SEQ ID NO: 3)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human IL15 nucleotide sequence (e.g., exon 1, exon 2, exon 3, exon 4, exon 5, exon 6, exon 7, exon 8, or NM_000585.4 (SEQ ID NO: 3)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse IL15 amino acid sequence (e.g., exon 1, exon 2, exon 3, exon 4, exon 5, exon 6, exon 7, exon 8, or NP_001241676.1 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse IL15 amino acid sequence (e.g., exon 1, exon 2, exon 3, exon 4, exon 5, exon 6, exon 7, exon 8, or NP_001241676.1 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human IL15 amino acid sequence (e.g., exon 1, exon 2, exon 3, exon 4, exon 5, exon 6, exon 7, exon 8, or NP_000576.1 (SEQ ID NO: 4)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human IL15 amino acid sequence (e.g., exon 1, exon 2, exon 3, exon 4, exon 5, exon 6, exon 7, exon 8, or NP_000576.1 (SEQ ID NO: 4)).

The present disclosure also provides an amino acid sequence, wherein the amino acid sequence is selected from the group consisting of:

a) an amino acid sequence shown in SEQ ID NO: 2 or 4;

b) an amino acid sequence having a homology of at least 90% with or at least 90% identical to the amino acid sequence shown in SEQ ID NO: 2 or 4;

c) an amino acid sequence encoded by a nucleic acid sequence, wherein the nucleic acid sequence is able to hybridize to a nucleotide sequence encoding the amino acid shown in SEQ ID NO: 2 or 4 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 2 or 4;

e) an amino acid sequence that is different from the amino acid sequence shown in SEQ ID NO: 2 or 4 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 2 or 4.

The present disclosure also relates to a nucleic acid (e.g., DNA or RNA) sequence, wherein the nucleic acid sequence can be selected from the group consisting of:

a) a nucleic acid sequence as shown in SEQ ID NO: 5, or a nucleic acid sequence encoding a homologous IL15 amino acid sequence of a humanized mouse;

b) a nucleic acid sequence that is shown in SEQ ID NO: 1, 3, 6, 9, 51;

c) a nucleic acid sequence that is able to hybridize to the nucleotide sequence as shown in SEQ ID NO: 1, 3, 5, 6, 9, or 51 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 1, 3, 5, 6 or 9;

e) a nucleic acid sequence that encodes an amino acid sequence, wherein the amino acid sequence has a homology of at least 90% with or at least 90% identical to the amino acid sequence shown in SEQ ID NO: 2 or 4;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 2 or 4;

g) a nucleic acid sequence that encodes an amino acid sequence, wherein the amino acid sequence is different from the amino acid sequence shown in SEQ ID NO: 2 or 4 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 2 or 4.

The present disclosure further relates to an IL15 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 1, 3, 5, 6, 9, or 51.

The disclosure also provides an amino acid sequence that has a homology of at least 90% with, or at least 90% identical to the sequence shown in SEQ ID NO: 2 or 4, and has protein activity. In some embodiments, the homology with the sequence shown in SEQ ID NO: 2 or 4 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 2 or 4 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 1, 3, 5, 6, 9, or 51 and encodes a polypeptide that has protein activity. In some embodiments, the homology with the sequence shown in SEQ ID NO: 1, 3, 5, 6, 9, or 51 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 1, 3, 5, 6, 9, or 51 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) IL15 from an endogenous non-human IL15 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous IL15 locus that comprises an exogenous sequence (e.g., a human sequence), e.g., an insertion of exogenous sequence or a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wild-type nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wild-type amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized IL15 gene or a humanized IL15 nucleic acid. In some embodiments, at least one or more portions of the gene or the nucleic acid is from the human IL15 gene, at least one or more portions of the gene or the nucleic acid is from a non-human IL15 gene. In some embodiments, the gene or the nucleic acid comprises a sequence that encodes a IL15 protein. The encoded IL15 protein is functional or has at least one activity of the human IL15 protein or the non-human IL15 protein, e.g., binding with human or non-human IL15 receptor, activating IL15 pathways, providing anti-apoptotic signals for T cells, inducing cell proliferation of natural kill cells, and/or activating NK cells.

In some embodiments, the chimeric protein or the chimeric polypeptide is a humanized IL15 protein or a humanized IL15 polypeptide. In some embodiments, at least one or more portions of the amino acid sequence of the protein or the polypeptide is from a human IL15 protein, and at least one or more portions of the amino acid sequence of the protein or the polypeptide is from a non-human IL15 protein. The humanized IL15 protein or the humanized IL15 polypeptide is functional or has at least one activity of the human IL15 protein or the non-human IL15 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized IL15 animal is made. For example, suitable mice for maintaining a xenograft, can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9): 3175-3182, 2002), NOD-Prkdc$^{scid}$ IL-2rg$^{null}$ mice (e.g., US20190320631, which is incorporated herein by reference in its entirety), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human IL15 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, NOD-Prkdc$^{scid}$IL-2rg$^{null}$ mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature IL15 coding sequence with human mature IL15 coding sequence. In some embodiments, the mouse can include an insertion of human mature IL15 coding sequence.

In some embodiments, the genetically-modified, non-human animal comprises a disruption in the animal's endogenous CD132 gene, wherein the disruption of the endogenous CD132 gene comprises deletion of exon 2 of the endogenous CD132 gene.

In some embodiments, the disruption of the endogenous CD132 gene further comprises deletion of exon 1 of the endogenous CD132 gene. In some embodiments, the disruption of the endogenous CD132 gene comprises deletion of part of exon 1 of the endogenous CD132 gene. In some embodiments, the disruption of the endogenous CD132 gene further comprises deletion of one or more exons or part of exons selected from the group consisting of exon 3, exon 4, exon 5, exon 6, exon 7, and exon 8 of the endogenous CD132 gene. In some embodiments, the disruption of the endogenous CD132 gene comprises deletion of exons 1-8 of the endogenous CD132 gene. In some embodiments, the disruption of the endogenous CD132 gene further comprises deletion of one or more introns or part of introns selected from the group consisting of intron 1, intron 2, intron 3, intron 4, intron 5, intron 6, and intron 7 of the endogenous CD132 gene. In some embodiments, the disruption consists of deletion of more than 150 nucleotides in exon 1; deletion of the entirety of intron 1, exon 2, intron 2, exon 3, intron 3, exon 4, intron 4, exon 5, intron 5, exon 6, intron 6, exon 7, intron 7; and deletion of more than 250 nucleotides in exon 8.

In some embodiments, the animal is homozygous with respect to the disruption of the endogenous CD132 gene. In some embodiments, the animal is heterozygous with respect to the disruption of the endogenous CD132 gene.

In some embodiments, the disruption prevents the expression of functional CD132 protein.

In some embodiments, the length of the remaining exon sequences at the endogenous CD132 gene locus is less than 30% of the total length of all exon sequences of the endogenous CD132 gene. In some embodiments, the length of the remaining sequences at that the endogenous CD132 gene locus is less than 15% of the full sequence of the endogenous CD132 gene.

In some embodiments, the animal is a CD132 knockout non-human animal, wherein the genome of the animal comprises from 5' to 3' at the endogenous CD132 gene locus, (a) a first DNA sequence; optionally (b) a second DNA sequence comprising an exogenous sequence; (c) a third DNA sequence, wherein the first DNA sequence, the optional second DNA sequence, and the third DNA sequence are linked, wherein the first DNA sequence comprises an endogenous CD132 gene sequence that is located upstream of intron 1, the second DNA sequence can have a length of 0 nucleotides to 300 nucleotides, and the third DNA sequence comprises an endogenous CD132 gene sequence that is located downstream of intron 7.

In some embodiments, the first DNA sequence comprises a sequence that has a length (5' to 3') of from 10 to 100 nucleotides (e.g., approximately 10, 20, 30, 40, 50, 60, 70, 80, 90, 100 nucleotides), wherein the length of the sequence refers to the length from the first nucleotide in exon 1 of the CD132 gene to the last nucleotide of the first DNA sequence.

In some embodiments, the first DNA sequence comprises at least 10 nucleotides from exon 1 of the endogenous CD132 gene. In some embodiments, the first DNA sequence has at most 100 nucleotides from exon 1 of the endogenous CD132 gene.

In some embodiments, the third DNA sequence comprises a sequence that has a length (5' to 3') of from 200 to 600 nucleotides (e.g., approximately 200, 250, 300, 350, 400, 450, 500, 550, 600 nucleotides), wherein the length of the sequence refers to the length from the first nucleotide in the third DNA sequence to the last nucleotide in exon 8 of the endogenous CD132 gene.

In some embodiments, the third DNA sequence comprises at least 300 nucleotides from exon 8 of the endogenous CD132 gene. In some embodiments, the third DNA sequence has at most 400 nucleotides from exon 8 of the endogenous CD132 gene.

In some embodiments, the animal is a genetically-modified, non-human animal produced by a method comprising knocking out one or more exons of endogenous CD132 gene by using (1) a first nuclease comprising a zinc finger protein, a TAL-effector domain, or a single guide RNA (sgRNA) DNA-binding domain that binds to a target sequence in exon 1 of the endogenous CD132 gene or upstream of exon 1 of the endogenous CD132 gene, and (2) a second nuclease comprising a zinc finger protein, a TAL-effector domain, or a single guide RNA (sgRNA) DNA-binding domain that binds to a sequence in exon 8 of the endogenous CD132 gene.

The animal with a disruption at CD132 gene is described in US20190320631, which is incorporated herein by reference in its entirety.

In some embodiments, the animal is a mammal, e.g., a monkey, a rodent, a rat, or a mouse. In some embodiments, the animal is a NOD mouse, a NOD/scid mouse, or a NOD/scid nude mouse. In some embodiments, the animal further comprises a disruption in the animal's endogenous Beta-2-Microglobulin (B2m) gene and/or a disruption in the animal's endogenous Forkhead Box N1 (Foxn1) gene.

Genetically modified non-human animals that comprise a modification of an endogenous non-human IL15 locus. In some embodiments, the modification can comprise a human nucleic acid sequence encoding at least a portion of a mature IL15 protein (e.g., at least 10%, 20%, 30%, 40%, 50%, 60%, 70%, 80%, 90%, 95%, 96%, 97%, 98%, or 99% identical to the mature IL15 protein sequence). Although genetically modified cells are also provided that can comprise the modifications described herein (e.g., ES cells, somatic cells), in many embodiments, the genetically modified non-human animals comprise the modification of the endogenous IL15 locus in the germline of the animal.

Genetically modified animals can express a human IL15 and/or a chimeric (e.g., humanized) IL15 from endogenous mouse loci, wherein the endogenous mouse IL15 gene locus has been inserted with a human IL15 gene and/or a nucleotide sequence that encodes a region of human IL15 sequence or an amino acid sequence that is at least 10%, 20%, 30%, 40%, 50%, 60%, 70&, 80%, 90%, 95%, 96%, 97%, 98%, or 99% identical to the human IL15 sequence. In various embodiments, an endogenous non-human IL15 locus is modified in whole or in part to comprise human nucleic acid sequence encoding at least one protein-coding sequence of a mature IL15 protein.

In some embodiments, the genetically modified mice express the human IL15 and/or chimeric IL15 (e.g., humanized IL15) from endogenous loci that are under control of mouse promoters and/or mouse regulatory elements. The modification at the endogenous mouse loci provide non-human animals that express human IL15 or chimeric IL15

(e.g., humanized IL15) in appropriate cell types and in a manner that does not result in the potential pathologies observed in some other transgenic mice known in the art. The human IL15 or the chimeric IL15 (e.g., humanized IL15) expressed in animal can maintain one or more functions of the wild-type mouse or human IL15 in the animal. For example, human or non-human IL15 receptors can bind to the expressed IL15, upregulate immune response, e.g., upregulate immune response by at least 10%, 20%, 30%, 40%, or 50%. Furthermore, in some embodiments, the animal does not express endogenous IL15. As used herein, the term "endogenous IL15" refers to IL15 protein that is expressed from an endogenous IL15 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human IL15 (NP_000576.1) (SEQ ID NO: 4).

The genome of the genetically modified animal can comprise an insertion at an endogenous IL15 gene locus a sequence encoding a human or chimeric IL15. In some embodiments, the sequence that is inserted at any endogenous IL15 gene locus, e.g., exon 1, exon 2, exon 3, exon 4, exon 5, exon 6, exon 7, exon 8, 5'-UTR, 3'-UTR, the first intron, the second intron, and the third intron, the fourth intron, the fifth intron, the sixth intron, the seventh intron, etc. In some embodiments, the sequence that is inserted is under the control of the regulatory region of the endogenous IL15 gene.

The genetically modified animal can have one or more cells expressing a human or chimeric IL15 (e.g., humanized IL15) that is at least 50%, 60%, 70%, 80%, 90%, 95%, 99% identical to human IL15. In some embodiments, the humanized IL15 has a sequence that has at least 10, 20, 30, 40, 50, 60, 70, 80, 90, 100, 110, 120, 130, 140, 150, or 160amino acids (e.g., contiguously or non-contiguously) that are identical to human IL15. Because human IL15 and non-human IL15 (e.g., mouse IL15) sequences, in many cases, are different, antibodies that bind to human IL15 will not necessarily have the same binding affinity with non-human IL15 or have the same effects to non-human IL15. Therefore, the genetically modified animal having a human or a humanized IL15 can be used to better evaluate the effects of anti-human IL15 antibodies in an animal model.

Furthermore, the genetically modified animal can be heterozygous with respect to the modification at the endogenous IL15 locus, or homozygous with respect to the modification at the endogenous IL15 locus.

In some embodiments, the humanized IL15 locus lacks a human IL15 5'-UTR. In some embodiment, the humanized IL15 locus comprises a rodent (e.g., mouse) 5'-UTR. In some embodiments, the humanization comprises a human 3'-UTR. In appropriate cases, it may be reasonable to presume that the mouse and human IL15 genes appear to be similarly regulated based on the similarity of their 5'-flanking sequence. As shown in the present disclosure, humanized IL15 mice that comprise a modification at an endogenous mouse IL15 locus, which retain mouse regulatory elements but comprise a humanization of IL15 encoding sequence, do not exhibit pathologies. Both genetically modified mice that are heterozygous or homozygous for humanized IL15 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized IL15 gene sequence.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized IL15 in the genome of the animal.

Figure 3:
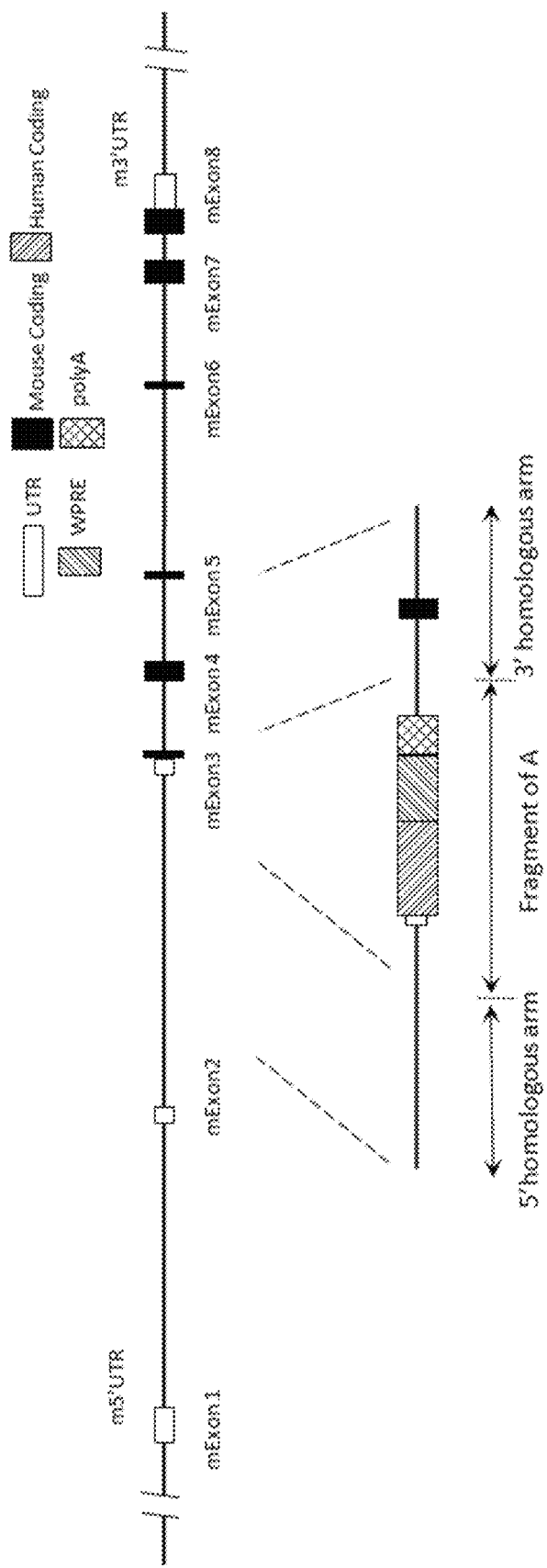
FIG. 3 is a schematic diagram showing an IL15 gene targeting strategy and the targeting plasmid.

In some embodiments, the non-human mammal comprises the genetic construct as described herein (e.g., gene construct as shown in FIG. 3). In some embodiments, a non-human mammal expressing human or humanized IL15 is provided. In some embodiments, the tissue-specific expression of human or humanized IL15 protein is provided.

In some embodiments, the expression of human or humanized IL15 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human IL15 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized IL15 protein.

In another aspect, the disclosure also provides a genetically-modified, non-human animal whose genome comprise a disruption in the animal's endogenous IL15 gene, wherein the disruption of the endogenous IL15 gene comprises deletion of exon 1, exon 2, exon 3, exon 4, exon 5, exon 6, exon 7, and/or exon 8, or part thereof of the endogenous IL15 gene.

In some embodiments, the disruption of the endogenous IL15 gene comprises deletion of one or more exons or part of exons selected from the group consisting of exon 1, exon 2, exon 3, exon 4, exon 5, exon 6, exon 7, and exon 8 of the endogenous IL15 gene.

In some embodiments, the disruption of the endogenous IL15 gene further comprises deletion of one or more introns or part of introns selected from the group consisting of intron 1, intron 2, intron 3, intron 4, intron 5, intron 6, and intron7 of the endogenous IL15 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous IL15 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, exon 8, intron 1, intron 2, intron 3, intron 4, intron 5, intron 6, and/or intron7 (e.g., deletion of at least 50 nucleotides of intron 2, exon 3, and at least 50 nucleotides of exon 3).

In another aspect, the disclosure further provides methods of determining toxicity of an agent (e.g., an IL15 antagonist or agonist). The methods involve administering the agent to the animal as described herein; and determining weight change of the animal. In some embodiments, the method further involve performing a blood test (e.g., determining red blood cell count).

The disclosure also relates to a method for establishing a genetically-modified non-human animal expressing two human or chimeric (e.g., humanized) genes. The method includes the steps of (a) using the method for establishing a IL15 gene humanized animal model to obtain a IL15 gene genetically modified humanized mouse;

(b) mating the IL15 gene genetically modified humanized mouse obtained in step (a) with another humanized mouse, and then screening to obtain a double humanized mouse model.

In some embodiments, in step (b), the IL15 gene genetically modified humanized mouse obtained in step (a) is mated with a PD-1 or PD-L1 humanized mouse to obtain a IL15 and PD-1 double humanized mouse model or a IL15 and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized IL15 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

The disclosure further relates to a IL15 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the IL15 gene function, human IL15 antibodies, the drugs or efficacies for human IL15 targeting sites, and the drugs for immune-related diseases and anti-tumor drugs.

Vectors

The present disclosure relates to a targeting vector, comprising: a) a DNA fragment homologous to the 5' end of a region to be altered (5' arm), which is selected from the IL15 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the IL15 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000074.6; c) the DNA fragment homologous to the 3' end of the region to be altered (3' arm) is selected from the nucleotide sequences that have at least 90% homology to the NCBI accession number NC_000074.6.

In some embodiments, a) the DNA fragment homologous to the 5' end of a region to be altered (5' arm) is selected from the nucleotides from the position 82347557 to the position 82346040 of the NCBI accession number NC_000074.6; c) the DNA fragment homologous to the 3' end of the region to be altered (3' arm) is selected from the nucleotides from the position 82344972 to the position 82343471 of the NCBI accession number NC_000074.6.

In some embodiments, the length of the selected genomic nucleotide sequence in the targeting vector can be more than about 1 kb, about 1.5 kb, about 2 kb, about 2.5 kb, about 3 kb, about 3.5 kb, about 4 kb, about 4.5 kb, about 5 kb, about 5.5 kb, or about 6 kb.

In some embodiments, the region to be altered is exon 1, exon 2, exon 3, exon 4, exon 5, exon 6, exon 7, and/or exon 8 of IL15 gene (e.g., exon 1, exon 2, exon 3, exon 4, exon 5, exon 6, exon 7, and/or exon 8 of mouse IL15 gene).

The targeting vector can further include a selected gene marker.

In some embodiments, the sequence of the 5' arm is shown in SEQ ID NO: 7; and the sequence of the 3' arm is shown in SEQ ID NO: 8.

In some embodiments, the sequence is derived from human (e.g., 375-863 of NM_000585.4). For example, the target region in the targeting vector is a part or entirety of the nucleotide sequence of a human IL15, preferably exon 1, exon 2, exon 3, exon 4, exon 5, exon 6, exon 7, and/or exon 8 of the human IL15. In some embodiments, the nucleotide sequence of the humanized IL15 encodes the entire or the part of human IL15 protein with the NCBI accession number NP_000576.1 (SEQ ID NO: 4).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous. In some embodiments, the non-human mammalian cell is a mouse cell. In some embodiments, the cell is a fertilized egg cell.

The disclosure also provides vectors for constructing a humanized animal model or a knock-out model. In some embodiments, the vectors comprise sgRNA sequence, wherein the sgRNA sequence target IL15 gene, and the sgRNA is unique on the target sequence of the gene to be altered, and meets the sequence arrangement rule of 5'-NNN (20)-NGG3' or 5'-CCN-N (20)-3'; and in some embodiments, the targeting site of the sgRNA in the mouse IL15 gene is located on the exon 1, exon 2, exon 3, exon 4, exon 5, exon 6, exon 7, exon 8, intron 1, intron 2, intron 3, intron 4, intron 5, intron 6, intron 7, upstream of exon 1, or downstream of exon 8 of the mouse IL15 gene. In some embodiments, the sgRNAs target intron 2 and/or intron 3.

In some embodiments, the 5' targeting sequence for the sequence is shown as SEQ ID NOS: 10-19, and the sgRNA sequence recognizes the 5' targeting site. In some embodiments, the 3' targeting sequence is shown as SEQ ID NOS: 20-28 and the sgRNA sequence recognizes the 3' targeting site. Thus, the disclosure provides sgRNA sequences for constructing a genetic modified animal model. In some embodiments, the oligonucleotide sgRNA sequences are set forth in SEQ ID NOS: 29-36.

In some embodiments, the disclosure relates to a plasmid construct (e.g., pT7-sgRNA) including the sgRNA sequence, and/or a cell including the construct.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides inserting in at least one cell of the animal, at an endogenous IL15 gene locus, a sequence encoding human or chimeric IL15. In some embodiments, the modification occurs in a germ cell, a somatic cell, a blastocyst, or a fibroblast, etc. The nucleus of a somatic cell or the fibroblast can be inserted into an enucleated oocyte.

FIG. 3 shows a humanization strategy for a mouse IL15 locus. In FIG. 3, the targeting strategy involves a vector comprising the 5' end homologous arm, mouse IL15 gene fragment, human IL15 gene fragment, WPRE, poly A signal sequence, mouse IL15 gene fragment, and 3' homologous arm. The process can involve replacing endogenous IL15 sequence with an exogenous sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous IL15 sequence with exogenous sequence.

Thus, in some embodiments, the methods for making a genetically modified, humanized animal, can include the step of replacing at an endogenous IL15 locus (or site), a nucleic acid encoding a sequence encoding a region of endogenous IL15 with a sequence encoding a human or chimeric IL15. The sequence can include a region (e.g., a part or the entire region) of exon 1, exon 2, exon 3, exon 4, exon 5, exon 6, exon 7, and/or exon 8 of a human IL15 gene. In some embodiments, the modified endogenous IL15 locus is exon 1, exon 2, exon 3, exon 4, exon 5, exon 6, exon 7, and/or exon 8 of mouse IL15 (e.g., exon 3).

In some embodiments, the methods of modifying an IL15 locus of a mouse to express a chimeric human/mouse IL15 peptide can include the steps of replacing at the endogenous mouse IL15 locus a nucleotide sequence encoding a mouse IL15 with a nucleotide sequence encoding a human IL15, thereby generating a sequence encoding a chimeric human/mouse IL15.

In some embodiments, the amino acid sequences as described herein do not overlap with each other.

The present disclosure further provides a method for establishing an IL15 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized IL15 protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized IL15, which are useful for testing agents that can decrease or block the interaction between IL15 and IL15 receptor, testing whether an agent can increase or decrease the immune response, and/or determining whether an agent is an IL15 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-IL15 antibody for the treatment of an immune disorder. The methods involve administering the anti-IL15 antibody (e.g., anti-human IL15 antibody) to the animal as described herein; and determining the inhibitory effects of the anti-IL15 antibody in the IL15 pathway activity. In some embodiments, the anti-IL15 antibody prevents IL15 from binding to IL15 receptor.

In some embodiments, the antibody is designed for treating various immune diseases or allergy (e.g., autoimmune disease, allergic rhinitis, rheumatoid arthritis, sinusitis, asthma, multiple sclerosis or eczema). Thus, the methods as described herein can be used to determine the effectiveness of an antibody in inhibiting immune response.

The present disclosure also provides methods of determining toxicity of an antibody (e.g., anti-IL15 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the IL15 gene function, human IL15 antibodies, drugs for human IL15 targeting sites, the drugs or efficacies for human IL15 receptor targeting sites, the drugs for immune-related diseases and antitumor drugs.

Genetically modified animals as described herein can also be used to provide a variety of uses that include, but are not limited to, establishing a human hemato-lymphoid animal model, developing therapeutics for human diseases and disorders, and assessing the efficacy of these therapeutics in the animal models.

In some embodiments, the genetically modified animals can be used for establishing a human hemato-lymphoid system. The methods involve engrafting a population of cells comprising human hematopoietic cells (CD34+ cells)

or human peripheral blood cells into the genetically modified animal described herein. In some embodiments, the methods further include the step of irradiating the animal prior to the engrafting. The human hemato-lymphoid system in the genetically modified animals can include various human cells, e.g., hematopoietic stem cells, myeloid precursor cells, myeloid cells, dendritic cells, monocytes, granulocytes, neutrophils, mast cells, lymphocytes, and platelets.

In some embodiments, the genetically modified animals can be used for reconstructing human immune system. The methods involve administering human hematopoietic stem cells to the animal as described herein, wherein the animal is irradiated; and determining the efficiency or success of reconstructing human immune system, e.g., evaluating T cell and NK cell development, proportion of CD45+ cells, and survival rate, etc.

In some embodiments, the animal after being engrafted with human hematopoietic stem cells or human peripheral blood cells to develop a human immune system has one or more of the following characteristics:

(a) the success rate of establishing a human hemato-lymphoid system is at least 30%, 40%, 50%, or 60% at week 4, 8, or 12;

(b) the percentage of human CD3+ cells is greater than 5%, 6%, 7%, 8%, 9%, 10% or %15 of human CD45+ cells in the animal; and (c) the percentage of human CD56+ cells is greater than 15%, 20%, 25%, or 30% of human CD45+ cells in the animal;

(d) at least 70%, 80%, or 90% of mice survived at or after day 40, 50, 60, 70, 80.

In some embodiments, the success of establishing a human hemato-lymphoid system is determined by having at least 25% human CD45+ cells in peripheral blood cells after being engrafted with human hematopoietic stem cells or human peripheral blood cells.

In some embodiments, the genetically modified animals have at least 10%, 20%, 30%, 40%, 50% human CD45+ cells after being engrafted with human hematopoietic stem cells or human peripheral blood cells (e.g., after 4, 5, 6, 7, 8, 9, 10, 11, or 12 weeks).

In some embodiments, the genetically modified animals have at least 10%, 20%, 30%, 40%, 50%, 60%, 70%, 80%, 90%, 1 fold, 2 folds, 5 folds, or 10 folds more human immune cells, including e.g., NK cells (e.g., hCD56+) and/or human T cells (e.g., hCD3+) than a NOD-Prkdc$^{scj}$-$_d$IL-2rg$^{null}$ mouse after being engrafted with human hematopoietic stem cells or human peripheral blood cells (e.g., after 4, 5, 6, 7, 8, 9, 10, 11, or 12 weeks).

In some embodiments, the genetically modified animals have a higher survival rate (e.g., at least 10%, 20%, 30%, 40%, 50%, 60%, 70%, 80%, 90% higher) than a NOD-Prkdcscid IL-2rgnull mouse after being engrafted with human hematopoietic stem cells or human peripheral blood cells (e.g., after 4, 5, 6, 7, 8, 9, 10, 11, or 12 weeks).

In some embodiments, the genetically modified animals can be used to determine the effectiveness of an agent or a combination of agents for the treatment of cancer. The methods involve engrafting tumor cells to the animal as described herein, administering the agent or the combination of agents to the animal; and determining the inhibitory effects on the tumors.

In some embodiments, the tumor cells are from a tumor sample obtained from a human patient. These animal models are also known as Patient derived xenografts (PDX) models. PDX models are often used to create an environment that resembles the natural growth of cancer, for the study of cancer progression and treatment. Within PDX models, patient tumor samples grow in physiologically-relevant tumor microenvironments that mimic the oxygen, nutrient, and hormone levels that are found in the patient's primary tumor site. Furthermore, implanted tumor tissue maintains the genetic and epigenetic abnormalities found in the patient and the xenograft tissue can be excised from the patient to include the surrounding human stroma. As a result, PDX models can often exhibit similar responses to anti-cancer agents as seen in the actual patient who provide the tumor sample.

While the genetically modified animals do not have functional T cells or B cells, the genetically modified animals still have functional phagocytic cells, e.g., neutrophils, eosinophils (*acidophilus*), basophils, or monocytes. Macrophages can be derived from monocytes, and can engulf and digest cellular debris, foreign substances, microbes, cancer cells. Thus, the genetically modified animals described herein can be used to determine the effect of an agent (e.g., anti-CD47 antibodies or anti-SIRPα antibodies) on phagocytosis, and the effects of the agent to inhibit the growth of tumor cells.

In some embodiments, human peripheral blood cells (hPBMC) or human hematopoietic stem cells (CD34+) are injected to the animal to develop human hematopoietic system. The genetically modified animals described herein can be used to determine the effect of an agent in human hematopoietic system, and the effects of the agent to inhibit tumor cell growth or tumor growth. Thus, in some embodiments, the methods as described herein are also designed to determine the effects of the agent on human immune cells (e.g., human T cells, B cells, or NK cells), e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer, or autoimmune diseases.

In some embodiments, the tested agent or the combination of tested agents is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the tested agent is designed for the treating melanoma, primary lung carcinoma, non-small cell lung carcinoma (NSCLC), small cell lung cancer (SCLC), primary gastric carcinoma, bladder cancer, breast cancer, and/or prostate cancer.

In some embodiments, the injected tumor cells are human tumor cells. In some embodiments, the injected tumor cells are melanoma cells, primary lung carcinoma cells, non-small cell lung carcinoma (NSCLC) cells, small cell lung cancer (SCLC) cells, primary gastric carcinoma cells, bladder cancer cells, breast cancer cells, and/or prostate cancer cells.

The inhibitory effects on tumors can also be determined by any methods known in the art. In some embodiments, the tumor cells can be labeled by a luciferase gene. Thus, the number of the tumor cells or the size of the tumor in the animal can be determined by an in vivo imaging system (e.g., the intensity of fluorescence). In some embodiments, the inhibitory effects on tumors can also be determined by measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the tested agent can be one or more agents selected from the group consisting of paclitaxel, cisplatin, carboplatin, pemetrexed, 5-FU, gemcitabine, oxaliplatin, docetaxel, and capecitabine.

In some embodiments, the tested agent can be an antibody, for example, an antibody that binds to CD47, PD-1, CTLA-4, LAG-3, TIM-3, BTLA, PD-L1, 4-1BB, CD27, CD28, CD47, TIGIT, CD27, GITR, or OX40. In some embodiments, the antibody is a human antibody.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

Genetically Modified Animal Model with Two or More Human or Chimeric Genes

The present disclosure further relates to methods for generating genetically modified animal model with two or more human or chimeric genes. The animal can comprise a human or chimeric IL15 gene and a sequence encoding an additional human or chimeric protein.

In some embodiments, the additional human or chimeric protein can further include e.g., Interleukin 33 (IL33), IL3, IL6, IL6R, IL15R, Granulocyte-macrophage colony-stimulating factor (GM-CSF), IL13, programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), CD137, TNF Receptor Superfamily Member 4 (TNFRSF4 or OX40), CD47 or SIRPα.

The methods of generating genetically modified animal model with two or more human or chimeric genes (e.g., humanized genes) can include the following steps:

(a) using the methods of introducing human IL15 gene or chimeric IL15 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric IL6, IL6R, IL33, IL13, IL15R, PD-1, CTLA-4, LAG-3, BTLA, PD-L1, CD27, CD28, TIGIT, TIM-3, GITR, OX40, CD137, CD47, or SIRPα. Some of these genetically modified non-human animal are described, e.g., in PCT/CN2017/090320, PCT/CN2017/099577, PCT/CN2017/110435, PCT/CN2017/099576, PCT/CN2017/099574, PCT/CN2017/106024, PCT/CN2017/110494, PCT/CN2017/110435, PCT/CN2017/117984, PCT/CN2018/081628, PCT/CN2017/120388, PCT/CN2017/099575, and PCT/CN2018/081629; each of which is incorporated herein by reference in its entirety.

In some embodiments, the IL15 humanization is directly performed on a genetically modified animal having a human or chimeric IL15R, PD-1, CTLA-4, BTLA, PD-L1, CD27, CD28, CD47, CD137, CD154, TIGIT, TIM-3, GITR, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of an agent or a combination therapy that targets two or more of these proteins, e.g., an IL15 and an additional therapeutic agent for the treatment of cancer. The methods include administering an agent or a combination of therapeutic agents to the animal, wherein the animal has a tumor; and determining the inhibitory effects of the combined treatment to the tumor. In some embodiments, the therapeutic agent is an antibody that specifically binds to PD-1, CTLA-4, BTLA, PD-L1, CD27, CD28, CD47, CD137, CD154, TIGIT, TIM-3, GITR, or OX40. In some embodiments, the additional therapeutic agent is an anti-CTLA4 antibody (e.g., ipilimumab), an anti-PD-1 antibody (e.g., nivolumab), or an anti-PD-L1 antibody. In some embodiments, the therapeutic agent is human IL15.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.
Materials and Methods
The following materials were used in the following examples.

NOD-Prkdc$^{scid}$Th-2rg$^{null}$ (B-NDG) mice were obtained from Beijing Biocytogen Co., Ltd. (Catalog Number: B-CM-001 or B-CM-002).

UCA kit was obtained from Beijing Biocytogen Co., Ltd. (Catalog Number: BCG-DX-001).

Ambion in vitro transcription kit was purchased from Ambion (Catalog number: AM1354).

Cas9mRNA was obtained from SIGMA (Catalog Number: CAS9MRNA-1EA).

BamHI, EcoRI, BbsI, and StuI restriction enzymes were purchased from NEB (Catalog numbers: R3136M, R3101M, R0539L and R0187M).

Example 1: IL15 Gene Humanized Mice

In this example, a non-human animal (such as a mouse) is modified so that the non-human animal contains a nucleic acid sequence encoding a human IL15 protein, and a genetically modified non-human animal can express human or humanized IL15 protein in the body. Schematic diagrams comparing the mouse IL15 gene (NCBI Gene ID: 16168, Primary source: MGI: 103014, UniProt ID: P48346; based on the transcript of NCBI accession number NM_001254747.1→NP_001241676.1, the mRNA sequence is provided in SEQ ID NO: 1, and the corresponding protein sequence is provided in SEQ ID NO: 2) and the human IL15 gene (NCBI Gene ID: 3600, Primary source: HGNC: 5977, UniProt ID: P40933; based on the transcript of NCBI accession number NM_000585.4→NP_000576.1, the mRNA sequence is provided in SEQ ID NO: 3, and the corresponding protein sequence is provided in SEQ ID NO: 4) are shown in FIG. 1.

Figure 2:
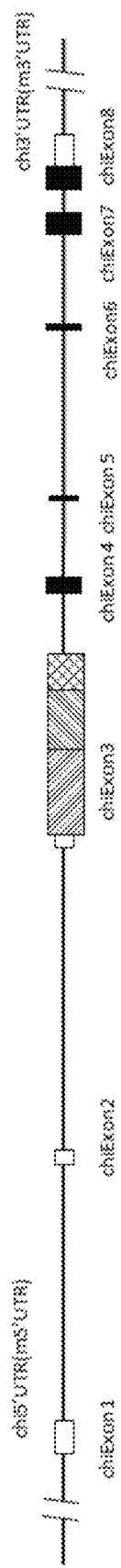
FIG. 2 is a schematic diagram showing humanized IL15 gene locus.

For the purpose of this experiment, a gene sequence encoding the human IL15 protein is introduced into the endogenous mouse IL15 locus, such that the mouse can express a human IL15 protein. For example, mouse cells can be modified by gene editing techniques, such as knocking in a sequence encoding human IL15 protein at the endogenous mouse IL-15 locus while disrupting the coding frame of mouse IL15 gene. The humanized mouse can express human IL15 protein and cannot express endogenous IL15 protein. In order to further increase the expression level of the IL15 protein, Woodchuck Hepatitis Virus (WHP) Posttranscriptional Regulatory Element (WPRE) and polyA (polyadenylation) signal sequences were added after the human IL15 coding sequence. As shown in FIG. 2, the mouse IL15 gene is not be transcribed or translated, due to the stop codon and the polyA signal at the end of the inserted sequence. The genetically modified humanized mouse IL15 gene locus is shown in FIG. 2. The mRNA sequence of humanized mouse IL15 gene is provided in SEQ ID NO: 5, and the DNA sequence of IL15 gene (chimeric IL15 gene DNA) is provided in SEQ ID NO: 6:

SEQ ID NO: 6

```
agcaacagaccttgatattttcattggtaaggtctactagtgtgtaacattttt gacagcaagactatccatatttgagatatttt gagcctgaatattttaatgaaatggagtttgatgggagtgtttaaacttcact tgttcccctgttttggtttagaaaaaaaatataattttg ttatatagaaaattcacaaatggtgttctcattaaactttattttaaagaacat acctaagacatctatgtgaagtctgtagatgaggct gttgttgtaaatttgactatcggatccagttggtggttatgtgaatctttgt atttgattgctcttattcaaattgagatggccctgaaacc tgtcagatctgggacactgtgtgaaataatggctttgttcttttattcagac aaacctggttttagtctgggcagtcatgggatttctat gacgccagatcagattttctaaatgatgctctcaggagggctaaatctgatg catgtgttaaggaacacagagcctaccctatgga aagcagatgtggcataagcaccaggcgtttctctatctgcttctggcttactc gcttgtgttttgatagtcatccttcatcctggttctgt tgcaggaagagttctggatggatggcagctggaagcccatcgccatagccag ctcatcttcaacattgaagctcttacctgggca ttaagtaATGAGAATTTCGAAACCACATTTGAGAAGTATTTCCATCCAGTGCTACTT

GTGTTTACTTCTAAACAGTCATTTTCTAACTGAAGCTGGCATTCATGTCTTCATT

TTGGGCTGTTTCAGTGCAGGGCTTCCTAAAACAGAAGCCAACTGGGTGAATGT
```

-continued

AATAAGTGATTTGAAAAAAATTGAAGATCTTATTCAATCTATGCATATTGATGCT

ACTTTATATACGGAAAGTGATGTTCACCCCAGTTGCAAAGTAACAGCAATGAA

GTGCTTTCTCTTGGAGTTACAAGTTATTTCACTTGAGTCCGGAGATGCAAGTAT

TCATGATACAGTAGAAAATCTGATCATCCTAGCAAACAACAGTTTGTCTTCTAA

TGGGAATGTAACAGAATCTGGATGCAAAGAATGTGAGGAACTGGAGGAAAAA

AATATTAAAGAATTTTTGCAGAGTTTTGTACATATTGTCCAAATGTTCATCAACA

CTTCTTGAaatcaacctctggattacaaaatttgtgaaagattgactggtattcttaactatgttgctccttttacgctatgtgga tacgctgctttaatgcctttgtatcatgctattgcttcccgtatggctttcattttctcctccttgtataaatcctggttgctgtctctttatga ggagttgtggcccgttgtcaggcaacgtggcgtggtgtgcactgtgtttgctgacgcaaccccactggttggggcattgccacc acctgtcagctcctttccgggactttcgctttccccctccctattgccacggcggaactcatcgccgcctgccttgcccgctgctgg acaggggctcggctgttgggcactgacaattccgtggtgttgtcggggaaatcatcgtcctttccttggctgctcgcctgtgttgcc acctggattctgcgcgggacgtccttctgctacgtccttcggccctcaatccagcggaccttccttcccgcggcctgctgccgg ctctgcggcctcttccgcgtcttcgccttcgccctcagacgagtcggatctcccttttgggccgcctccccgcATCGATACC

GTCGACCTCGACTGTGCCTTCTAGTTGCCAGCCATCTGTTGTTTGCCCCTCCCC

CGTGCCTTCCTTGACCCTGGAAGGTGCCACTCCCACTGTCCTTTCCTAATAAA

ATGAGGAAATTGCATCGCATTGTCTGAGTAGGTGTCATTCTATTCTGGGGGGTG

GGGTGGGGCAGGACAGCAAGGGGGAGGATTGGGAAGACAATAGCAGGCATG

CTGGGGAaaatagcatatggcttttcttataaggtcaccttaatctcagttctactttataataagtcgcatgattactctctaaac atctctggctgcgacagatatgtttctccaagatttatcttgattttaaaaataagtagcatgggctttggaaaacaagactagcagta tgcctgtattattgtgccattgttaaggtgttattacacttcactcagtctcttttgttctctaaatgtctattcacttcgcacattgtgtctc tgagggcaaggtctggtgctaggcatctttcagcagagtctacacagagtacagacttctggtgtttaaggtgttgactgacgctg ctctctgtaactataaaatctctgacagcactgacaagtcaggtcagagaattaaaactgtgtctatctcagacaaataaggtccta aataaccaaattaagttttcatgtaggagctgttagaatgaaaaaggatatacttcttttttgagacaggatttcataactatgtagcgtt gggtggcctggaactcaccagggtagtcctgagcttacagaatcccttgttcctgtctctctcatcctaggtccgacgaggcctac atcaatcctagccctggcccaaatacttttactggtttaaattttatccagttttttctctgtgtgataatatgtattttaatttccatatacttg tatgaaatgaatgtaaaactagtgtgatgctattgtgtgacattactaatctatgctgtttataatgtgtagtctattaataaagacaga agggcaagaggaagaggataatgacagaaaaagctcagtagtcccaagagtatacatgtcagtcattaagaatgtcagtttatca ttgaccttcaattggagaaatggctactggagat only lists the DNA sequences involved in the modified region, in which the single underlined region is a nucleic acid sequence encoding human IL15 protein (referred to as a humanized sequence, SEQ ID NO:51), the wavy underlined region is WPRE, and the double-underlined region is the polyA signal.

The targeting strategy is shown in FIG. 3, wherein the targeting vector comprises an upstream and a downstream homologous arm for the mouse IL15 gene, a fragment containing a human sequence encoding human IL15 protein, and WPRE and polyA sequences (together referred to as "A fragment"). The upstream arm (5' homologous arm, SEQ ID NO: 7) is identical to nucleotide sequence of 82347557-82346040 of the NCBI accession number NC_000074.6; the downstream arm (3' homologous arm, SEQ ID NO: 8) is identical to nucleotide sequence of 82344972-82343471 of the NCBI accession number NC_000074.6; and the A fragment (SEQ ID NO: 9) includes the following: a mouse genomic DNA located within exon 3 of mouse IL15 gene (identical to nucleotide sequence 82364039-82345612 of the NCBI accession number NC_000074.6), a human IL15 gene coding sequence (identical to nucleotide sequence of 375-863 of the NCBI accession number NM_000585.4), WPRE, polyA, and a mouse genomic DNA located within introns 3-4 of the mouse IL15 gene (identical to nucleotide sequence 82345579-82344973 of the NCBI accession number NC_000074.6). The targeting vector was synthesized (using the pUC57 plasmid as a backbone plasmid). Multiple pUC57-IL15 plasmids were obtained. After sequences were verified by sequencing, the plasmid with correct sequences was used in the subsequent experiments.

The target sequences of sgRNAs determine the targeting specificity and Cas9 cleavage efficiency at the gene of interest. Based on the targeting strategy, sgRNA sequences recognizing the 5' end targeting site (sgRNA1-sgRNA10) and the 3' end targeting site (sgRNA11-sgRNA19) were designed and synthesized. The 5' end targeting site and the 3' end targeting site are located in the intron 2 and intron 3 of the mouse IL15 gene, respectively. The targeting site sequences on IL15 for each sgRNA are shown below:

```
sgRNA-1 target sequence (SEQ ID NO: 10):
5'-ttgtaaatttgactatcagttgg-3' sgRNA-2 target sequence (SEQ ID NO: 11):
5'-acagtcattgcgggctgagtggg-3' sgRNA-3 target sequence (SEQ ID NO: 12):
5'-gagaggctggtttacacctaggg-3' sgRNA-4 target sequence (SEQ ID NO: 13):
5'-ctagatccccaagtggtgaaagg-3' sgRNA-5 target sequence (SEQ ID NO: 14):
5'-taaatttgactatcagttggtgg-3' sgRNA-6 target sequence (SEQ ID NO: 15):
5'-gttcaggggacttaggctttagg-3' sgRNA-7 target sequence (SEQ ID NO: 16):
5'-taagtccctgaacccacaatgg-3' sgRNA-8 target sequence (SEQ ID NO: 17):
5'-cgttccctgtgaccctgg-3' sgRNA-9 target sequence (SEQ ID NO: 18):
5'-ttcatacctggtaaatgttagg-3' sgRNA-10 target sequence (SEQ ID NO: 19):
5'-acaaacttaggccatggaactgg-3' sgRNA-11 target sequence (SEQ ID NO: 20):
5'-ggattgatgtcgtcggacctagg-3' sgRNA-12 target sequence (SEQ ID NO: 21):
5'-agggctaggattgatgtcgtcgg-3' sgRNA-13 target sequence (SEQ ID NO: 22):
5'-cataactatgtagcgttgggtgg-3' sgRNA-14 target sequence (SEQ ID NO: 23):
5'-atttcataactatgtagcgttgg-3' sgRNA-15 target sequence (SEQ ID NO: 24):
5'-gacgacatcaatcctagccctgg-3' sgRNA-16 target sequence (SEQ ID NO: 25):
5'-aaagtatttgggccagggctagg-3' sgRNA-17 target sequence (SEQ ID NO: 26):
5'-ttcgcacattgtgtctctgaggg-3' sgRNA-18 target sequence (SEQ ID NO: 27):
5'-ctacacagagtacagacttctgg-3' sgRNA-19 target sequence (SEQ ID NO: 28):
5'-attttaaaaataagtagcatggg-3'
```

Figure 4A:
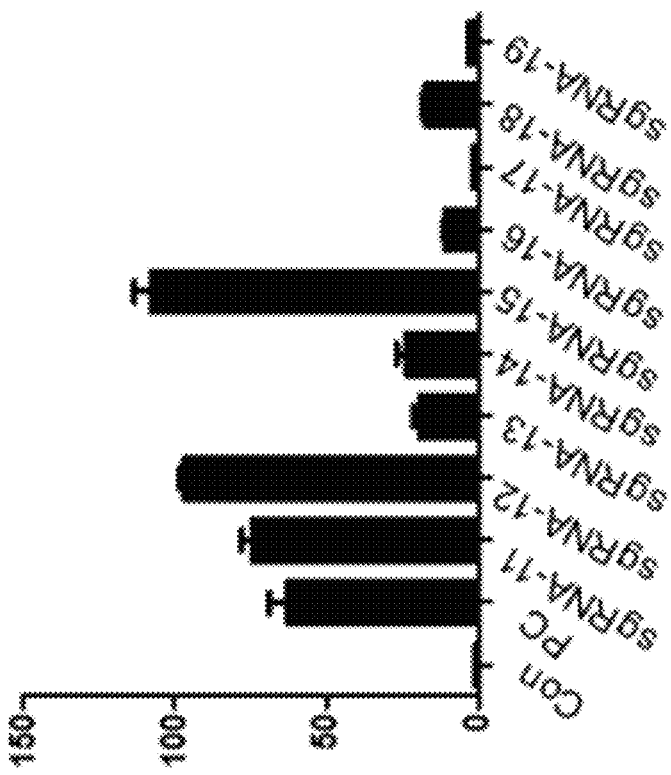
FIG. 4A a histogram showing activity testing results for sgRNA1-sgRNA10. Con is a negative control; PC is a positive control.
Figure 4B:
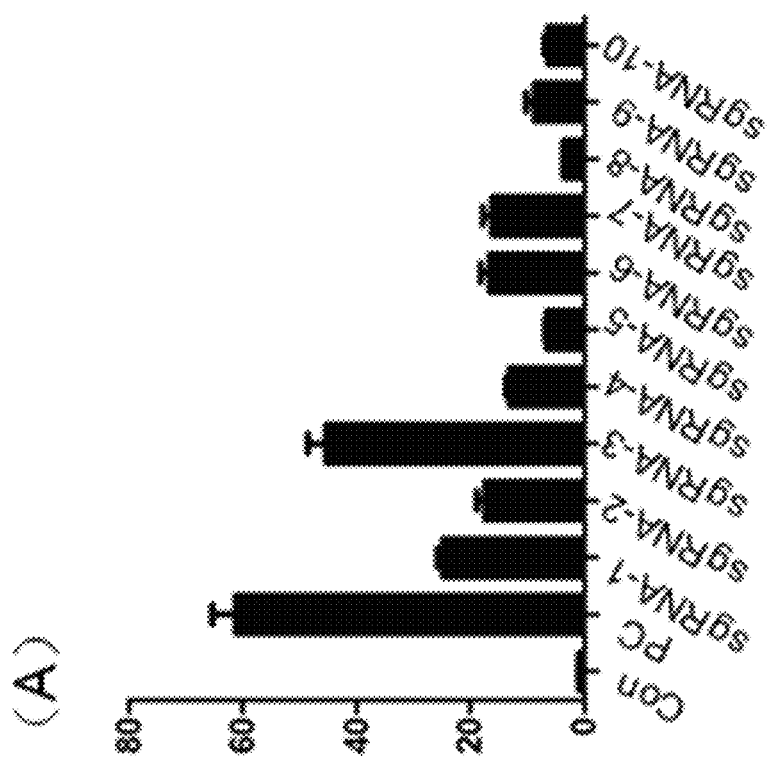
FIG. 4B is a histogram showing activity testing results for sgRNA11-sgRNA19. Con is a negative control; PC is a positive control.

The UCA kit was used to detect the activities of sgRNAs. The results showed that the guide sgRNAs had different activities (see Table 3 and FIGS. 4A-4B). sgRNA-1 and sgRNA-12 were selected for subsequent experiments because of their efficiency. Restriction enzyme cleavage sites were added to the 5' end and the complementary strand to obtain a forward oligonucleotide and a reverse oligonucleotide (see Table 4 for the sequence). After annealing, the annealing products were ligated to the pT7-sgRNA plasmid (the plasmid was first linearized with BbsI) to obtain expression vectors pT7-IL15-1 and pT7-IL15-12.

TABLE 3 sgRNA activity test results

| 5' end targeting site test results | | 3' end targeting site test results | |
|---|---|---|---|
| Con. | 1.00 ± 0.15 | Con. | 1.00 ± 0.16 |
| PC | 61.18 ± 7.15 | PC | 62.66 ± 10.70 |
| sgRNA-1 | 24.75 ± 1.78 | sgRNA-11 | 74.53 ± 5.85 |
| sgRNA-2 | 17.40 ± 2.49 | sgRNA-12 | 96.85 ± 3.22 |
| sgRNA-3 | 45.34 ± 5.56 | sgRNA-13 | 19.51 ± 3.51 |
| sgRNA-4 | 13.10 ± 1.12 | sgRNA-14 | 23.94 ± 5.46 |
| sgRNA-5 | 6.63 ± 0.57 | sgRNA-15 | 107.71 ± 10.24 |
| sgRNA-6 | 16.59 ± 2.86 | sgRNA-16 | 10.98 ± 0.68 |
| sgRNA-7 | 16.21 ± 2.77 | sgRNA-17 | 1.89 ± 0.24 |
| sgRNA-8 | 3.63 ± 0.15 | sgRNA-18 | 17.38 ± 2.41 |
| sgRNA-9 | 8.77 ± 2.54 | sgRNA-19 | 3.53 ± 0.23 |
| sgRNA-10 | 6.34 ± 1.38 | / | / |

TABLE 4 sgRNA-1 and sgRNA-12 sequences

| sgRNA-1 sequence | | |
|---|---|---|
| SEQ ID NO: 29 | | Upstream:<br>5'-TTGTAAATTTGACTATCAGT-3' |
| SEQ ID NO: 30 | (forward oligonucleotide) | Upstream:<br>5'-TAGGTTGTAAATTTGACTATCAGT-3' |
| SEQ ID NO: 31 | | Downstream:<br>5'-ACTGATAGTCAAATTTACAA-3' |
| SEQ ID NO: 32 | (reverse oligonucleotide) | Downstream:<br>5'-AAACACTGATAGTCAAATTTACAA-3' |
| sgRNA-12 sequence | | |
| SEQ ID NO: 33 | | Upstream:<br>5'-AGGGCTAGGATTGATGTCGT-3' |
| SEQ ID NO: 34 | (forward oligonucleotide) | Upstream:<br>5'-TAGGAGGGCTAGGATTGATGTCGT-3' |
| SEQ ID NO: 35 | | Downstream:<br>5'-ACGACATCAATCCTAGCCCT-3' |
| SEQ ID NO: 36 | (reverse oligonucleotide) | Downstream:<br>5'-AAACGACATCAATCCTAGCCCT-3' |

The pT7-sgRNA vector was synthesized. The vector has a DNA fragment containing the T7 promoter and sgRNA scaffold (SEQ ID NO: 37), and was ligated to the backbone vector (Takara, Catalog number: 3299) by restriction enzyme digestion (EcoRI and BamHI). The plasmids were confirmed by sequencing.

The pre-mixed Cas9 mRNA, pUC57-IL15 plasmid and in vitro transcription products of pT7-IL15-1, pT7-IL15-12 plasmids were injected into the cytoplasm or nucleus of B-NDG mouse fertilized eggs (NOD/scid background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation).

Figure 5A:
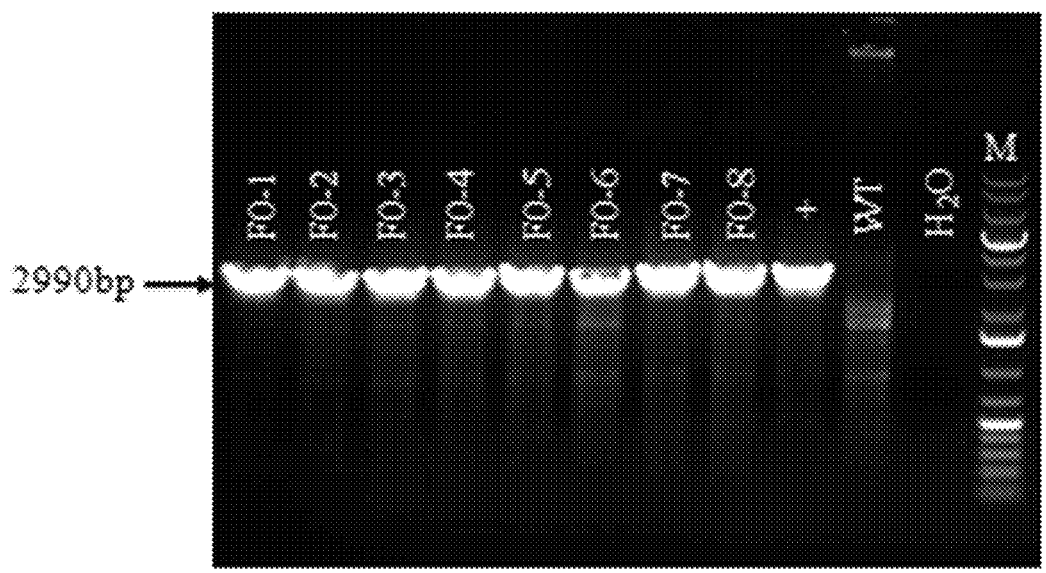
FIG. 5A shows PCR identification results of samples collected from tails of F0 generation mice. 5' end primer pairs (L-GT-F/WPRE-R2) were used for amplification. WT is wild-type. $H_2O$ is a blank control, + is a positive control and M is the Marker.
Figure 5B:
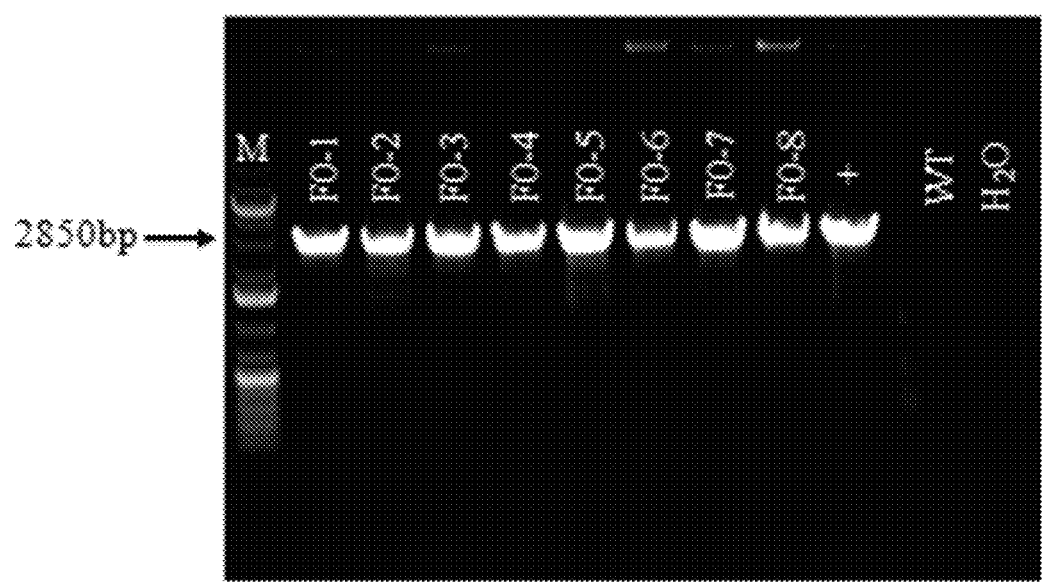
FIG. 5B shows PCR identification results of samples collected from tails of F0 generation mice. 3' end primer pairs (WPRE-F2/R-GT-R) were used for amplification. WT is wild-type. $H_2O$ is a blank control, + is a positive control and M is the Marker.

The genotype of somatic cells of F0 generation mice can be identified by PCR. The identification results of some F0 generation mice are shown in FIGS. 5A-5B. The results of the 5' end primer detection and the 3' end primer detection shows that the eight mice numbered F0-1 to F0-8 in FIGS. 5A-5B were all positive clones. The PCR analysis was performed using the following primers:

```
5' end primers:
L-GT-F (SEQ ID NO: 38):
5'-GGGCACCAGCCACCTATTTTGATGA-3'

WPRE-R2 (SEQ ID NO: 39):
5'-ATCCAGGTGGCAACACAGGC-3'

3' end primers:
WPRE-F2 (SEQ ID NO: 40):
5'-TGCACTGTGTTTGCTGACGC-3'

R-GT-R (SEQ ID NO: 41):
5'-AAACCAAGCTCTTTGGAGGAGGGTG-3'
```

Figures 6A, 6B:
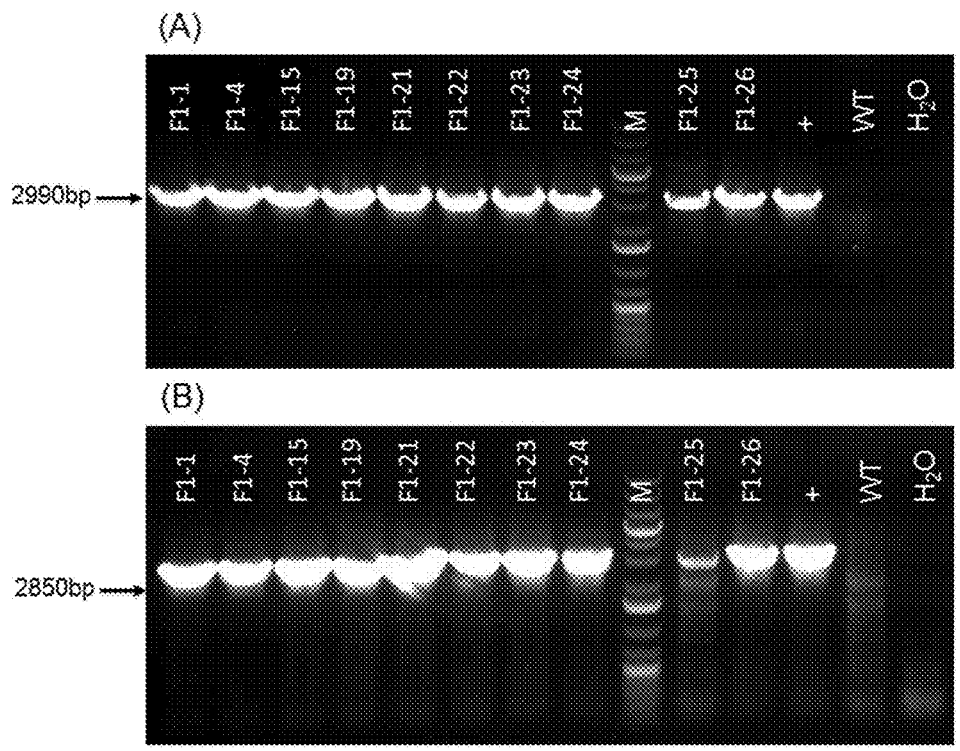
FIG. 6A shows PCR identification results of samples collected from tails of F1 generation mice. 5' end primer pairs (L-GT-F/WPRE-R2) were used for amplification. WT is wild-type. $H_2O$ is a blank control, + is a positive control and M is the Marker.
FIG. 6B shows PCR identification results of samples collected from tails of F1 generation mice. 3' end primer pairs (WPRE-F2/R-GT-R) were used for amplification. WT is wild-type. $H_2O$ is a blank control, + is a positive control and M is the Marker.

The positive F0 generation mice were mated with B-NDG mice to obtain F1 generation mice. The same PCR method was used to identify the genotypes of the F1 mice, and the results of some F1 mice were shown in FIGS. 6A-6B. Ten F1 mice that were identified as positive by PCR were further tested by Southern blot to determine whether there were random insertions. Genomic DNA was collected from mouse tail. The sample was digested by StuI restriction enzyme, and then was transferred to a membrane and hybridized with probes. Probes P1 and P2 are located in the 3' homologous arm and in the inserted WPRE sequence, respectively. The following primers were used in the experiment:

```
P1-F (SEQ ID NO: 42):
5'-TTGCCCTCCAGTGGCTCACTATTTC-3'

P1-R (SEQ ID NO: 43):
5'-ACATATTGAGAGACCGCCTGACCCT-3'

P2-F (SEQ ID NO: 44):
5'-GTGGATACGCTGCTTTAATGCC-3'

P2-R (SEQ ID NO: 45):
5'-AAGGGAGATCCGACTCGTCT-3'
```

Figure 7:
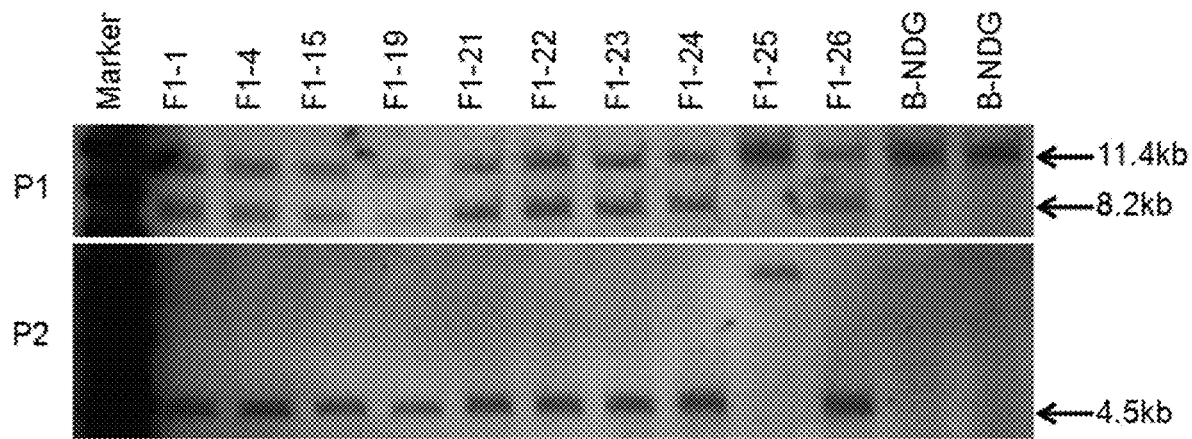
FIG. 7 is an image showing Southern blot results. The P1 panel shows the P1 probe detection results, and the P2 panel shows the P2 probe detection results. M is the Marker.

Southern blot detection results are shown in FIG. 7. Based on the results using P1 and P2 probes, no random insertion was detected in all of the 10 mice except F1-25. The results confirmed that the remaining 9 mice were positive heterozygotes with no random insertions. The 9 positive mice were F1-1, F1-4, F1-15, F1-19, F1-21, F1-22, F1-23, F1-24 and F1-26. The results indicated that this method can be used to construct genetically engineered IL15 gene humanized mice without random insertions.

The expression of humanized IL15 protein in positive clone mice can be confirmed by routine detection methods, such as using ELISA. One IL15 gene humanized mouse prepared by this method and one B-NDG mouse were selected, and 7.5 µg/200 µl of anti-mCD3e antibody was injected to each mouse intraperitoneally. About 1.5 hours after the stimulation, the mouse spleen was collected and grinded for ELISA detection. In B-NDG mice, no human IL15 was detected. In the humanized IL15 mice, human IL15 was detected.

In addition, Cas9 can cause double strand breakage in genomic DNA. Insertion/deletion mutations can be randomly generated by repairing through chromosomal homologous recombination. The method can also generate IL15 knockout mice, and the gene deletions can be detected by routine PCR method. A pair of primers was designed, which are located to the left of the 5' end of the targeting site and to the right of the 3' end of the targeting site. The primer sequences are as follows:

```
Upstream primer (SEQ ID NO: 46):
5'-gctatgcatcaagcttggtaccgataccagtgaactggaaagcc
atggtc-3'

Downstream primer (SEQ ID NO: 47):
5'-aataacttaatcgtggaggatgatcctcttcctcttgcccttct
gtctt-3'
```

Figure 8:
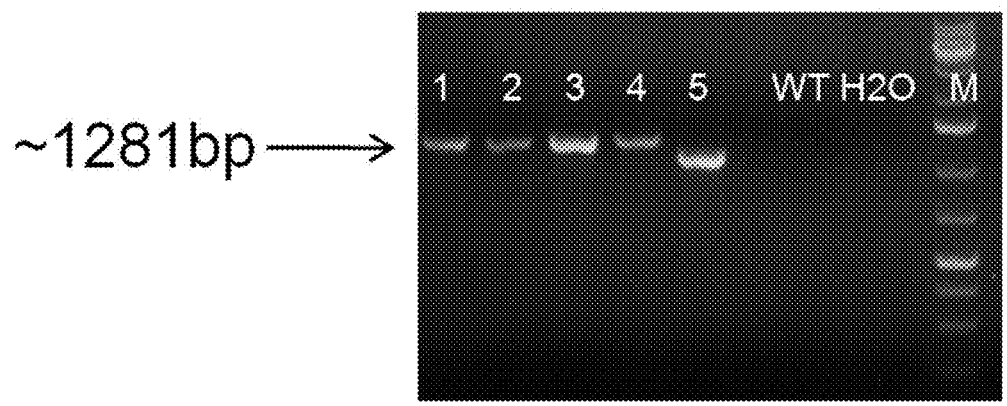
FIG. 8 shows PCR identification results of samples collected from tails of IL15 gene knockout mice. M is the Marker, $H_2O$ is a blank control, WT is the B-NDG mice. Mice with numbers 1-5 showed different degrees of gene deletion.

The test results are shown in FIG. 8. The mice numbered 1, 2, 3, 4, and 5 all had different degrees of gene deletion, and they were further confirmed as IL15 knockout mice by sequencing.

Example 2: Double- or Multiple-Gene Humanized Mice Containing Humanized IL15 Gene Mice with the humanized IL15 gene prepared using the methods as described in the present disclosure can also be used to prepare an animal model with double-humanized or multi-humanized genes. For example, the fertilized egg cells used in microinjection and embryo transfer can be selected from fertilized egg cells from other genetically modified mice. For example, CSF2 (or IL3, CSF1) and IL15 double gene humanized mouse models can be obtained by gene editing of fertilized egg cells from CSF2 (or IL3, CSF1) humanized mice using the methods described herein. In addition, the genetically engineered IL15 gene humanized animal model homozygote or heterozygote can be mated with other genetically modified homozygous or heterozygous animal models, and the progeny can be screened. According to the Mendel's law, there is a chance to obtain double-gene or multiple-gene modified heterozygous mice, and then the heterozygous animals can be further mated with each other to finally obtain the double-gene or multiple-gene modified homozygous mice. For example, the CSF2 humanized mouse can be obtained by modifying the mouse stem cell by gene editing. After the endogenous mouse CSF2 start codon (ATG), the entire coding frame of the mouse CSF2 gene was replaced with a sequence encoding the human CSF2 protein (SEQ ID NO: 48). The humanized mouse can express the human CSF2 protein in vivo and does not express endogenous CSF2 protein. CSF1 and IL3 humanized mice can be obtained using the same strategy. The human CSF1 protein coding sequence for replacement is shown in SEQ ID NO: 49. After replacement, the humanized mouse can express human CSF1 protein and do not express endogenous CSF1 protein. The human IL3 protein coding sequence for replacement is shown in SEQ ID NO: 50. After replacement, the humanized mouse can express human IL3 protein and do not express endogenous IL3 protein.

Example 3: Immune System Reconstruction

Figure 9:
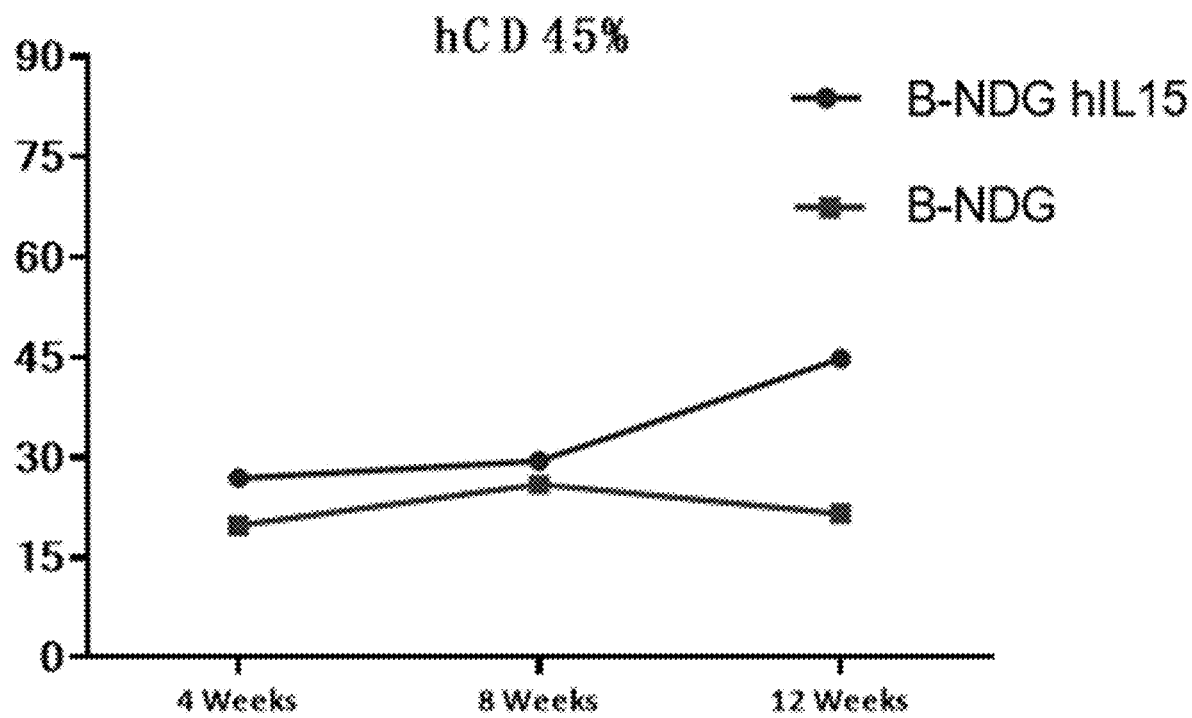
FIG. 9 is a graph showing the average percentage of CD45+ cells within living cells in peripheral blood detected from genetically engineered IL15 gene humanized mice (or B-NDG hIL15 for short) and B-NDG mice.
Figure 10:
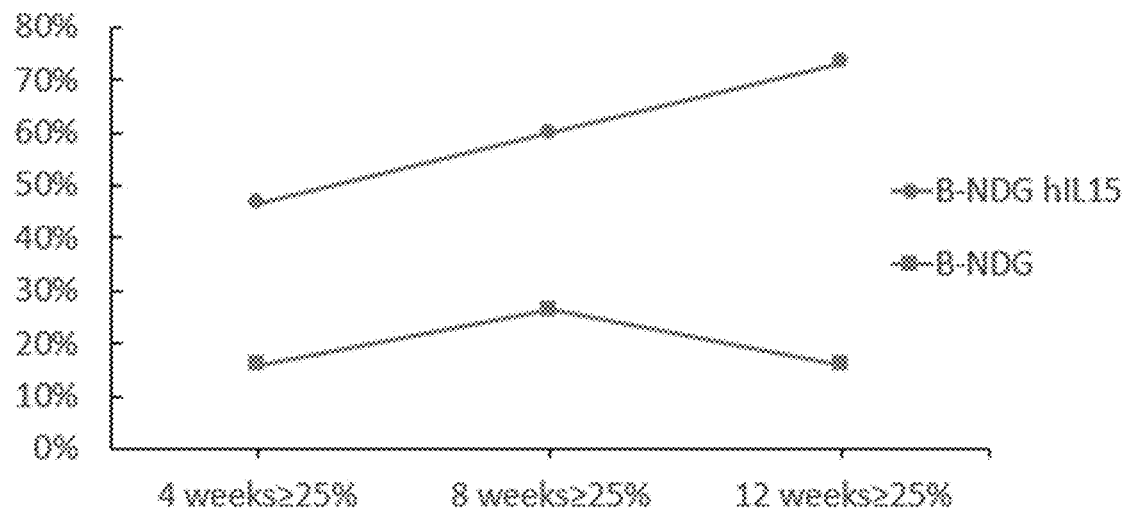
FIG. 10 is a graph showing the success rate of reconstructed human hematopoietic stem cell (CD34+) from B-NDG hIL15 mice and B-NDG mice.
Figure 11:
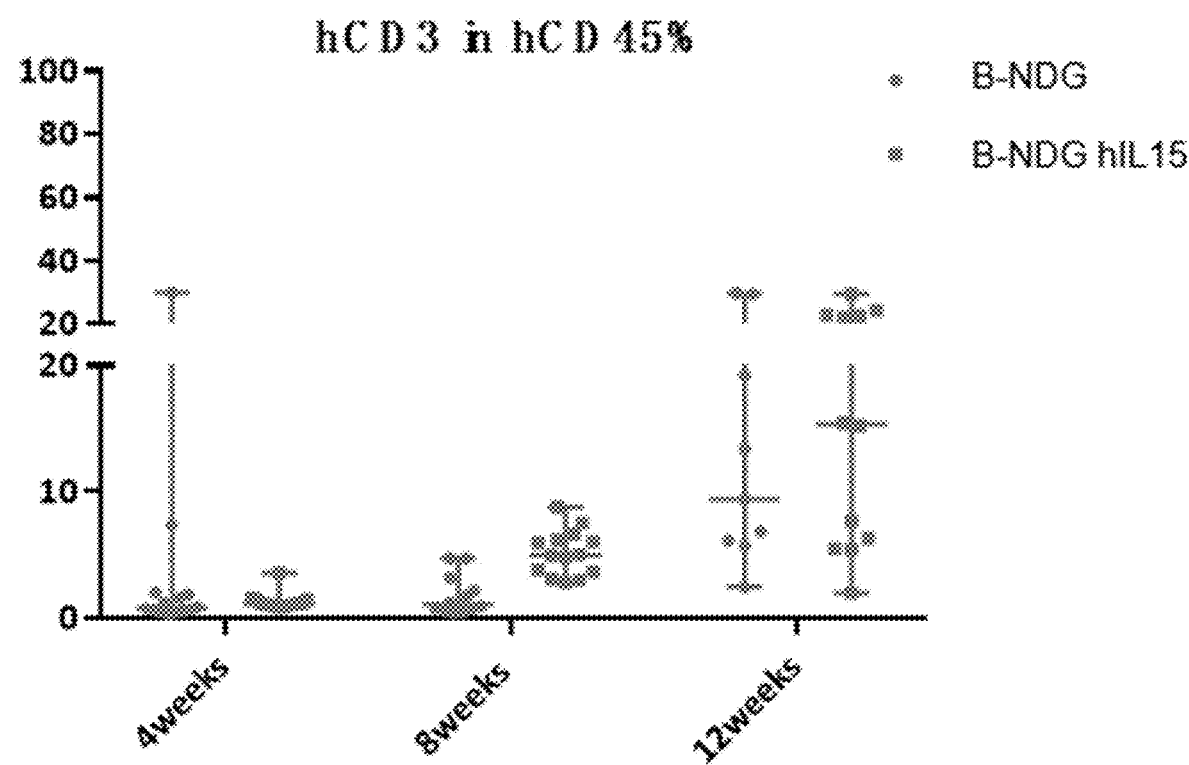
FIG. 11 is a graph showing the percentage of hCD3 within human leukocyte in human hematopoietic stem cell (CD34+) reconstructed B-NDG hIL15 mice and B-NDG mice.
Figure 12:
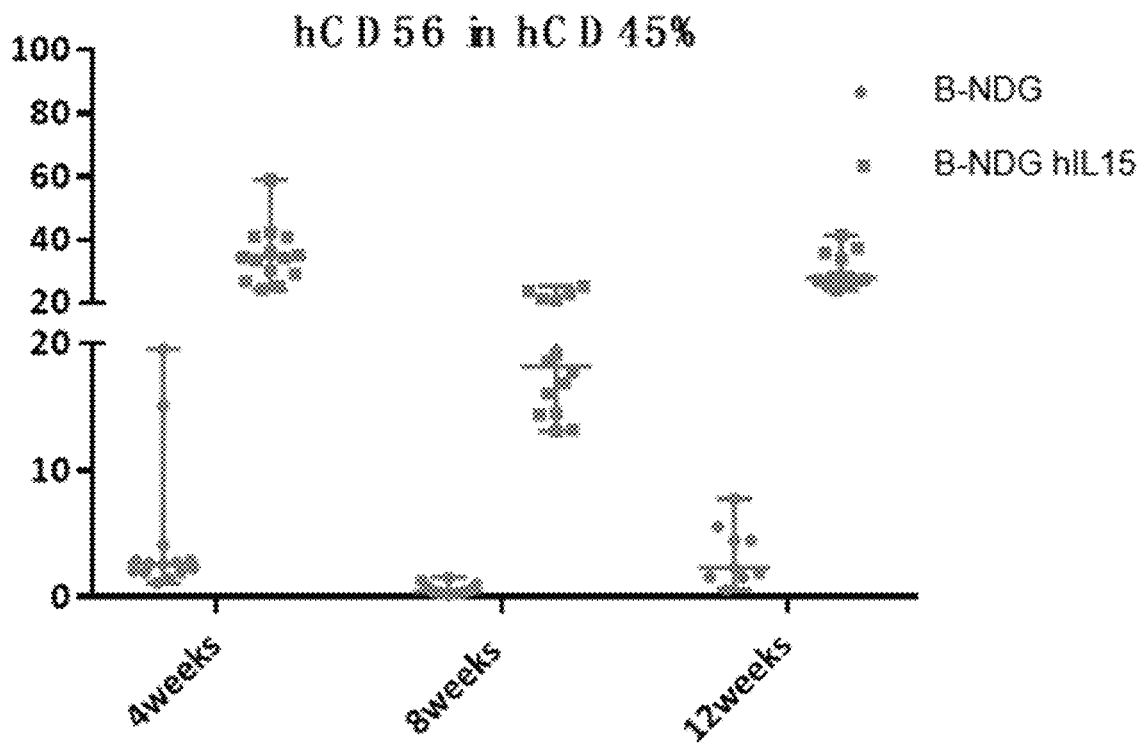
FIG. 12 is a graph showing the percentage of hCD56 within human leukocyte in human hematopoietic stem cell (CD34+) reconstructed B-NDG hIL15 mice and B-NDG mice.
Figure 13:
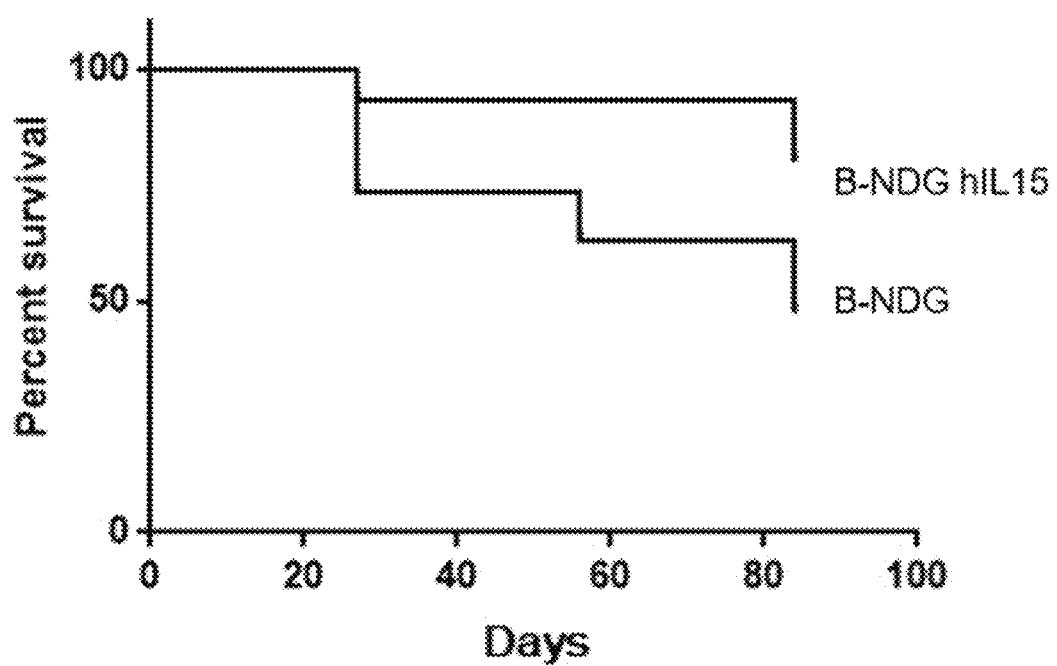
FIG. 13 is a graph showing the survival rate of human hematopoietic stem cell (CD34+) reconstructed B-NDG hIL15 mice and B-NDG mice.

The genetically engineered IL15 gene humanized mice (6 weeks old, B-NDG background, n=15) and B-NDG mice (n=19) were selected. After irradiation (2.0 Gy), $1.5 \times 10^5$ human hematopoietic stem cells (CD34+) were injected through tail vein to reconstruct the immune system in mice. The criterion for successful reconstruction is that human CD45 cells account for at least 25% of total living cells in peripheral blood. Peripheral blood (PB) was taken every four weeks after the transplantation for flow cytometry analysis to assess if the reconstruction was successful, and survival rate of the mice was also recorded. Flow cytometry results showed that cells expressing human leukocyte surface molecular markers (CD45+) could be detected in all immuno-deficient mice. However, the proportion of CD45+ cells and the number of successful reconstruction in IL-15 humanized mice were significantly higher than those of the B-NDG mice (see FIGS. 9-10). In addition, T cells (CD3+) and NK cells (CD56+) were also higher in the IL15 humanized mice (FIGS. 11-12). The survival rate of the IL15 humanized mice was also higher during the experiment period (FIG. 13). This indicated that the IL15 gene humanized mice can effectively promote the development of human T cells and NK cells in vivo, and improve the immune reconstruction success rate.

Example 4. Methods Based on Embryonic Stem Cell Technologies

The non-human mammals described herein can also be prepared through other gene editing systems and approaches, including but not limited to: gene homologous recombination based on embryonic stem cells (ES), zinc finger nuclease (ZFN), transcriptional activator-like effector factor nuclease (TALEN), homing endonuclease (megakable base ribozyme), or some other techniques. The example herein uses the traditional ES cell gene homologous recombination as an example to explain how to prepare and obtain IL15 gene humanized mice by some other methods.

Based on the gene editing strategy as shown in FIGS. 2-3, a new recombinant vector is designed. The experiment is designed to destroy mouse IL15 gene coding frame and to insert into the mouse IL15 locus a nucleic acid sequence encoding human IL15 protein. The recombinant vector includes a 5' homologous arm, a 3' homologous arm and a sequence fragment from human IL15. The vector can also contain a resistance gene for positive clone screening, such as neomycin phosphotransferase coding sequence Neo. On both sides of the resistance gene, two site-specific recombination sequences in the same orientation, such as Frt or LoxP, can be added. Furthermore, a negative screening marker, such as the diphtheria toxin A subunit coding gene (DTA), can be added downstream of the recombinant vector 3' homologous arm.

Vector construction can be carried out using methods known in the art, such as enzyme digestion. The recombinant vector with correct sequence can be used to transfect mouse embryonic stem cells, and the cells transfected with the recombinant vector are next screened by using the positive clone marker gene. Southern Blot can be used to detect DNA recombination. Positive clones are selected. The positive clone cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The chimeric blastocysts following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected for subsequent breeding and identification. The gene recombination is detected by PCR. The F1 generation mice are obtained by mating the F0 generation chimeric mice with wild-type mice. F1 heterozygous mice are selected by performing PCR on samples collected from mouse tails. Next, the F1 heterozygous mice can be mated to each other to obtain F2 generation homozygous mice. In addition, the F1 heterozygous mice can also be mated with Flp or Cre mice to remove the positive clone screening marker gene (e.g., Neo), and then the IL15 humanized homozygous mice can be obtained by mating these mice with each other.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified, non-human animal, wherein the genome of the animal comprises an endogenous IL15 gene locus, wherein the endogenous IL15 gene locus comprises:
   an insertion of an exogenous sequence comprising a human IL15 polypeptide coding sequence; and
   exons 4-8 of the endogenous IL15 gene, wherein the animal has one or more cells expressing the human IL15 polypeptide, wherein the animal in its genome comprises a sequence that is at least 80% identical to SEQ ID NO: 6.

2. The animal of claim 1, wherein the human IL15 polypeptide coding sequence encodes an amino acid sequence that is at least 90% identical to SEQ ID NO: 4.

3. The animal of claim 1, wherein the exogenous sequence comprises a Woodchuck Hepatitis Virus (WHP) Posttranscriptional Regulatory Element (WPRE) sequence and a polyA (polyadenylation) signal sequence.

4. The animal of claim 1, wherein the exogenous sequence is operably linked to an endogenous regulatory element at the endogenous IL15 gene locus.

5. The animal of claim 1, wherein the exogenous sequence is operably linked to an endogenous 5'-UTR at the endogenous IL15 gene locus.

6. The animal of claim 1, wherein the animal is a mammal.

7. The animal of claim 1, wherein the animal does not express endogenous IL15.

8. The animal of claim 1, wherein the animal in its genome comprises from 5' to 3' mouse exon 1, mouse intron 1, mouse exon 2, mouse intron 2, a part of mouse exon 3, a sequence encoding the human IL15 polypeptide, a part of mouse intron 3, mouse exon 4, mouse intron 4, mouse exon 5, mouse intron 5, mouse exon 6, mouse intron 6, mouse exon 7, mouse intron 7, and mouse exon 8.

9. The animal of claim 1, wherein the animal is a NOD-Prkdc$^{scid}$IL-2rg$^{null}$ mouse.

10. The animal of claim 1, wherein the animal further comprises a sequence encoding an additional human or chimeric protein.

11. The animal of claim 10, wherein the additional human or chimeric protein is programmed cell death protein 1 (PD-1), cytotoxic T-lymphocyte-associated protein 4 (CTLA-4), Lymphocyte Activating 3 (LAG-3), IL15 receptor, B And T Lymphocyte Associated (BTLA), Programmed Cell Death 1 Ligand 1 (PD-L1), CD3, CD27, CD28, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα) or TNF Receptor Superfamily Member 4 (OX40).

12. A method of determining effectiveness of an anti-IL15 antibody in treating an immune disorder, comprising:
   administering the anti-IL15 antibody to the animal of claim 1; and
   determining effects of the anti-IL15 antibody in treating the immune disorder.

13. A method of determining effectiveness of an agent or a combination of agents for treating cancer, comprising:
   engrafting tumor cells to the animal of claim 1, thereby forming one or more tumors in the animal;
   administering the agent or the combination of agents to the animal; and
   determining inhibitory effects on the tumors.

14. A genetically-modified, non-human animal whose genome comprises at least one chromosome comprising an exogenous sequence encoding a human IL15 polypeptide, wherein the human IL15 polypeptide comprises a sequence that is a least 80% identical to SEQ ID NO: 4, wherein the animal has one or more cells expressing the human IL15 polypeptide, wherein the animal in its genome comprises a sequence that is at least 80% identical to SEQ ID NO: 6.

15. The animal of claim 14, wherein the animal in its genome comprises a sequence that is at least 90% identical to SEQ ID NO: 6.

16. The animal of claim 14, wherein the animal in its genome comprises SEQ ID NO: 6.

17. The animal of claim 1, wherein the human IL15 polypeptide comprises a human signal peptide sequence.

18. The animal of claim 1, wherein the exogenous sequence is inserted at exon 3 of the endogenous IL15 gene.

19. The animal of claim 1, wherein the endogenous IL15 gene locus comprises a deletion of one or more nucleotides at exon 3 or intron 3 of the endogenous IL15 gene.

20. The animal of claim 1, wherein the animal in its genome comprises a sequence that is at least 90% identical to SEQ ID NO: 6.

21. The animal of claim 1, wherein the animal in its genome comprises SEQ ID NO: 6.

22. The animal of claim 1, wherein the animal is a mouse.

* * * * *

SEQUENCE LISTING

```
<160> NUMBER OF SEQ ID NOS: 51

<210> SEQ ID NO 1
<211> LENGTH: 1287
<212> TYPE: DNA
<213> ORGANISM: Mus musculus

<400> SEQUENCE: 1
ttcttgacca agacttcaat actcagtggc actgtattcc ccttctgtcc agccactctt      60
ccccagagtt ctcttcttca tcctcccact tgcagagtag ggcagcttgc aggtcctcct     120
gcaagtctct cccaattctc tgcgcccaaa agacttgcag tgcatctcct tacgcgctgc     180
agggaccttg ccagggcagg actgccccg cccagttgca gagttggacg aagacgggat      240
cctgctgtgt ttggaaggct gagttccaca tctaacagct cagagagaat ccaccttgac     300
acatggccct ctggctcttc aaagcactgc ctcttcatgg tccttgctgg tgaggtcctt     360
aagaacacag aaacccatgt cagcagataa ccagcctaca ggaggccaag aagagttctg     420
```

```
gatggatggc agctggaagc ccatcgccat agccagctca tcttcaacat tgaagctctt    480
acctgggcat taagtaatga aaattttgaa accatatatg aggaatacat ccatctcgtg    540
ctacttgtgt ttccttctaa acagtcactt tttaactgag gctggcattc atgtcttcat    600
tttgggctgt gtcagtgtag gtctccctaa acagaggcc aactggatag atgtaagata    660
tgacctggag aaaattgaaa gccttattca atctattcat attgacacca ctttatacac    720
tgacagtgac tttcatccca gttgcaaagt tactgcaatg aactgctttc tcctggaatt    780
gcaggttatt ttacatgagt acagtaacat gactcttaat gaaacagtaa gaaacgtgct    840
ctaccttgca aacagcactc tgtcttctaa caagaatgta gcagaatctg gctgcaagga    900
atgtgaggag ctggaggaga aaaccttcac agagttttg caaagcttta tacgcattgt     960
ccaaatgttc atcaacacgt cctgactgca tgcgagcctc ttccgtgttt ctgttattaa    1020
ggtacctcca cctgctgctc agaggcagca cagctccatg catttgaaat ctgctgggca    1080
aactaagctt cctaacaagg agataatgag ccacttggat cacatgaaat cttggaaatg    1140
aagagaggaa aagagctcgt ctcagactta tttttgcttg cttatttta atttattgct     1200 tcatttgtac atatttgtaa tataacagaa gatgtggaat aaagttgtat ggatattta    1260 tcaattgaaa tttaaaaaaa aaaaaaa                                        1287
```

<210> SEQ ID NO 2
<211> LENGTH: 162
<212> TYPE: PRT
<213> ORGANISM: Mus musculus

<400> SEQUENCE: 2

```
Met Lys Ile Leu Lys Pro Tyr Met Arg Asn Thr Ser Ile Ser Cys Tyr
 1               5                  10                  15

Leu Cys Phe Leu Leu Asn Ser His Phe Leu Thr Glu Ala Gly Ile His
             20                  25                  30

Val Phe Ile Leu Gly Cys Val Ser Val Gly Leu Pro Lys Thr Glu Ala
         35                  40                  45

Asn Trp Ile Asp Val Arg Tyr Asp Leu Glu Lys Ile Glu Ser Leu Ile
     50                  55                  60

Gln Ser Ile His Ile Asp Thr Thr Leu Tyr Thr Asp Ser Asp Phe His
 65                  70                  75                  80

Pro Ser Cys Lys Val Thr Ala Met Asn Cys Phe Leu Leu Glu Leu Gln
                 85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser
```

<210> SEQ ID NO 3
<211> LENGTH: 2012
<212> TYPE: DNA
<213> ORGANISM: Homo sapiens

<400> SEQUENCE: 3

```
gttgggactc cgggtggcag gcgcccgggg gaatcccagc tgactcgctc actgccttcg      60
aagtccggcg ccccccggga gggaactggg tggccgcacc ctcccggctg cggtggctgt     120
cgccccccac cctgcagcca ggactcgatg gagaatccat tccaatatat ggccatgtgg     180
ctctttggag caatgttcca tcatgttcca tgctgctgac gtcacatgga gcacagaaat     240
caatgttagc agatagccag cccatacaag atcgtattgt attgtaggag gcattgtgga     300
tggatggctg ctggaaaccc cttgccatag ccagctcttc ttcaatactt aaggatttac     360
cgtggctttg agtaatgaga atttcgaaac cacatttgag aagtatttcc atccagtgct     420
acttgtgttt acttctaaac agtcattttc taactgaagc tggcattcat gtcttcattt     480
tgggctgttt cagtgcaggg cttcctaaaa cagaagccaa ctgggtgaat gtaataagtg     540
atttgaaaaa aattgaagat cttattcaat ctatgcatat tgatgctact ttatatacgg     600
aaagtgatgt tcaccccagt tgcaaagtaa cagcaatgaa gtgctttctc ttggagttac     660
aagttatttc acttgagtcc ggagatgcaa gtattcatga tacagtagaa atctgatca     720
tcctagcaaa caacagtttg tcttctaatg ggaatgtaac agaatctgga tgcaaagaat     780
gtgaggaact ggaggaaaaa aatattaaag aattttgca gagttttgta catattgtcc     840
aaatgttcat caacacttct tgattgcaat tgattctttt taaagtgttt ctgttattaa     900
caaacatcac tctgctgctt agacataaca aaacactcgg catttcaaat gtgctgtcaa     960
aacaagtttt tctgtcaaga agatgatcag accttggatc agatgaactc ttagaaatga    1020
aggcagaaaa atgtcattga gtaatatagt gactatgaac ttctctcaga cttactttac    1080
tcattttttt aatttattat tgaaattgta catatttgtg gaataatgta aaatgttgaa    1140
taaaaatatg tacaagtgtt gttttttaag ttgcactgat attttacctc ttattgcaaa    1200
atagcatttg tttaagggtg atagtcaaat tatgtattgg tggggctggg taccaatgct    1260
gcaggtcaac agctatgctg gtaggctcct gccagtgtgg aaccactgac tactggctct    1320
cattgacttc cttactaagc atagcaaaca gaggaagaat ttgttatcag taagaaaaag    1380
aagaactata tgtgaatcct cttctttata ctgtaattta gttattgatg tataaagcaa    1440
ctgttatgaa ataagaaat tgcaataact ggcatataat gtccatcagt aaatcttggt    1500
ggtggtggca ataataaact tctactgata ggtagaatgg tgtgcaagct tgtccaatca    1560
cggattgcag gccacatgcg gcccaggaca actttgaatg tggcccaaca caaattcata    1620
aactttcata catctcgttt ttagctcatc agctatcatt agcggtagtg tatttaaagt    1680
gtggcccaag acaattcttc ttattccaat gtggcccagg gaaatcaaaa gattggatgc    1740
ccctggtata gaaaactaat agtgacagtg ttcatatttc atgctttccc aaatacaggt    1800
atttttatttt cacattcttt ttgccatgtt tatataataa taaagaaaaa ccctgttgat    1860
ttgttggagc cattgttatc tgacagaaaa taattgttta tatttttgc actacactgt    1920
ctaaaattag caagctctct tctaatggaa ctgtaagaaa gatgaaatat ttttgtttta    1980
ttataaattt atttcacctt aaaaaaaaaa aa                                   2012
```

<210> SEQ ID NO 4
<211> LENGTH: 162
<212> TYPE: PRT
<213> ORGANISM: Homo sapiens

<400> SEQUENCE: 4

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65              70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 5
<211> LENGTH: 1802
<212> TYPE: DNA
<213> ORGANISM: Artificial Sequence
<220> FEATURE:
<223> OTHER INFORMATION: Humanized IL 15

<400> SEQUENCE: 5

```
ttcttgacca agacttcaat actcagtggc actgtattcc ccttctgtcc agccactctt      60
ccccagagtt ctcttcttca tcctccccct tgcagagtag ggcagcttgc aggtcctcct     120
gcaagtctct cccaattctc tgcgcccaaa gacttgcagt gcatctcct  tacgcgctgc     180 agggaccttg ccagggcagg actgcccccg cccagttgca gagttggacg aagacgggat     240
cctgctgtgt ttggaaggct gagttccaca tctaacagct cagagagaat ccaccttgac     300
acatggccct ctggctcttc aaagcactgc ctcttcatgg tccttgctgg tgaggtcctt     360
aagaacacag aaacccatgt cagcagataa ccagcctaca ggaggccaag aagagttctg     420
gatggatggc agctggaagc ccatcgccat agccagctca tcttcaacat gaagctctt      480 acctgggcat taagtaatga gaatttcgaa accacatttg agaagtattt ccatccagtg     540
ctacttgtgt ttacttctaa acagtcattt tctaactgaa gctggcattc atgtcttcat     600
tttgggctgt tcagtgcagg gcttcctaa  aacagaagcc aactgggtga atgtaataag     660
tgatttgaaa aaattgaag atcttattca atctatgcat attgatgcta ctttatatac     720
ggaaagtgat gttcaccccca gttgcaaagt aacagcaatg aagtgctttc tcttggagtt     780
acaagttatt tcacttgagt ccggagatgc aagtattcat gatacagtag aaaatctgat     840
catcctagca acaacagtt  tgtcttctaa tgggaatgta acagaatctg gatgcaaaga     900
atgtgaggaa ctgaggaaaa aaatattaa  agaattttg cagagttttg tacatattgt     960
ccaaatgttc atcaacactt cttgaaatca acctctggat tacaaaattt gtgaaagatt    1020
```

```
gactggtatt cttaactatg ttgctccttt tacgctatgt ggatacgctg ctttaatgcc    1080
tttgtatcat gctattgctt cccgtatggc tttcattttc tcctccttgt ataaatcctg    1140
gttgctgtct ctttatgagg agttgtggcc cgttgtcagg caacgtggcg tggtgtgcac    1200
tgtgtttgct gacgcaaccc ccactggttg gggcattgcc accacctgtc agctcctttc    1260
cgggactttc gctttccccc tcctattgc cacggcggaa ctcatcgccg cctgccttgc     1320
ccgctgctgg acaggggctc ggctgttggg cactgacaat tccgtggtgt tgtcggggaa    1380
atcatcgtcc tttccttggc tgctcgcctg tgttgccacc tggattctgc gcgggacgtc    1440
cttctgctac gtcccttcgg ccctcaatcc agcggacctt ccttcccgcg gcctgctgcc    1500
ggctctgcgg cctcttccgc gtcttcgcct tcgccctcag acgagtcgga tctcccttt g   1560
ggccgcctcc ccgcatcgat accgtcgacc tcgactgtgc cttctagttg ccagccatct    1620
gttgtttgcc cctccccgt gccttccttg accctggaag gtgccactcc cactgtcctt     1680
tcctaataaa atgaggaaat tgcatcgcat tgtctgagta ggtgtcattc tattctgggg    1740
ggtggggtgg ggcaggacag caaggggag gattgggaag acaatagcag gcatgctggg     1800
ga                                                                   1802

<210> SEQ ID NO 6
<211> LENGTH: 2943
<212> TYPE: DNA
<213> ORGANISM: Artificial Sequence
<220> FEATURE:
<223> OTHER INFORMATION: Humanized IL 15

<400> SEQUENCE: 6
agcaacagac cttgatattt tcattggtaa ggtctactag tgtgtaacat ttttgacagc      60
aagactatcc atatttgaga tattttgagc ctgaatattt taatgaaatg gagtttgatg     120
ggagtgttta aacttcactt gttccctgt tttggtttag aaaaaaaata taattttgtt      180
atatagaaaa ttcacaaatg gtgttctcat taaactttat tttaaagaac atacctaaga    240
catctatgtg aagtctgtag atgaggctgt tgttgtaaat ttgactatcg gatccagttg    300
gtggttatgt gaatctttgt atttgattgc tcttattcaa attgagatgg ccctgaaacc    360
tgtcagatct gggacactgt gtgaaataat ggctttgttc ttttattcag acaaacctgg   420
ttttagtctg ggcagtcatg ggatttctat gacgccagat cagattttct aaatgatgct   480
ctcaggaggg ctaaatctga tgcatgtgtt aaggaacaca gagcctaccc tatggaaagc    540
agatgtggca taagcaccag gcgtttctct atctgcttct ggcttactcg cttgtgtttt    600
gatagtcatc cttcatcctg gttctgttgc aggaagagtt ctggatggat ggcagctgga    660
agcccatcgc catagccagc tcatcttcaa cattgaagct cttacctggg cattaagtaa    720
tgagaatttc gaaaccacat tgagaagta tttccatcca gtgctacttg tgtttacttc     780
taaacagtca ttttctaact gaagctggca ttcatgtctt cattttgggc tgtttcagtg    840
cagggcttcc taaaacagaa gccaactggg tgaatgtaat aagtgatttg aaaaaaattg    900
aagatcttat tcaatctatg catattgatg ctactttata tacggaaagt gatgttcacc    960
ccagttgcaa agtaacagca atgaagtgct ttctcttgga gttacaagtt atttcacttg   1020
agtccggaga tgcaagtatt catgatacag tagaaaatct gatcatccta gcaaacaaca   1080
gtttgtcttc taatgggaat gtaacagaat ctggatgcaa agaatgtgag gaactggagg   1140
aaaaaaatat taagaatttt tgcagagtt tgtacatat tgtccaaatg ttcatcaaca     1200
cttcttgaaa tcaacctctg gattacaaaa tttgtgaaag attgactggt attcttaact   1260
```

| | |
|---|---|
| atgttgctcc ttttacgcta tgtggatacg ctgctttaat gcctttgtat catgctattg | 1320 |
| cttcccgtat ggctttcatt ttctcctcct tgtataaatc ctggttgctg tctctttatg | 1380 |
| aggagttgtg gcccgttgtc aggcaacgtg gcgtggtgtg cactgtgttt gctgacgcaa | 1440 |
| cccccactgg ttggggcatt gccaccacct gtcagtcct ttccgggact ttcgctttcc | 1500 |
| ccctccctat tgccacggcg gaactcatcg ccgcctgcct tgcccgctgc tggacagggg | 1560 |
| ctcggctgtt gggcactgac aattccgtgg tgttgtcggg gaaatcatcg tcctttcctt | 1620 |
| ggctgctcgc ctgtgttgcc acctggattc tgcgcgggac gtccttctgc tacgtccctt | 1680 |
| cggccctcaa tccagcggac cttccttccc gcggcctgct gccggctctg cggcctcttc | 1740 |
| cgcgtcttcg ccttcgccct cagacgagtc ggatctccct ttgggccgcc tccccgcatc | 1800 |
| gataccgtcg acctcgactg tgccttctag ttgccagcca tctgttgttt gcccctcccc | 1860 |
| cgtgccttcc ttgaccctgg aaggtgccac tcccactgtc ctttcctaat aaaatgagga | 1920 |
| aattgcatcg cattgtctga gtaggtgtca ttctattctg gggggtgggg tgggcagga | 1980 |
| cagcaagggg gaggattggg aagacaatag caggcatgct ggggaaaata gcatatggct | 2040 |
| tttcttataa ggtcaccta atctcagttc tactttataa taagtcgcat gattactctc | 2100 |
| taaacatctc tggctgcgac agatatgttt ctccaagatt tatcttgatt ttaaaaataa | 2160 |
| gtagcatggg ctttggaaaa caagactagc agtatgcctg tattctttgt gccattgtta | 2220 |
| aggtgttatt acacttcact cagtctcttt tgttctctaa atgtctattc acttcgcaca | 2280 |
| ttgtgtctct gagggcaagg tctggtgcta ggcatctttc agcagagtct acacagagta | 2340 |
| cagacttctg gtgtttaagg tgttgactga cgctgctctc tgtaactata aaatctctga | 2400 |
| cagcactgac aagtcaggtc agagaattaa aactgtgtct atctcagaca ataaggtcc | 2460 |
| taaataacca aattaagttt tcatgtagga gctgttagaa tgaaaagga tatacttctt | 2520 |
| tttgagacag gatttcataa ctatgtagcg ttgggtggcc tggaactcac cagggtagtc | 2580 |
| ctgagcttac agaatccctt gttcctgtct ctctcatcct aggtccgacg aggcctacat | 2640 |
| caatcctagc cctggcccaa atacttttac tggtttaaat tttatccagt ttttctctgt | 2700 |
| gtgataatat gtattttaat ttccatatac ttgtatgaaa tgaatgtaaa actagtgtgc | 2760 |
| ttgctattgt gtgacattac taatctatgc tgttttataat gtgtagtcta ttaataaaga | 2820 |
| cagaagggca agaggaagag gataatgaca gaaaaagctc agtagtccca agagtataca | 2880 |
| tgtcagtcat taagaatgtc agtttatcat tgaccttcaa ttggagaaat ggctactgga | 2940 |
| gat | 2943 |

<210> SEQ ID NO 7
<211> LENGTH: 1500
<212> TYPE: DNA
<213> ORGANISM: Mus musculus

<400> SEQUENCE: 7

| | |
|---|---|
| atgcgctact tattacctgg ccattggtag aaaattactt taatttgtac agtaatgata | 60 |
| actgttatct cctactttc tgccataaat gaacgcttgg gtggacatag tcttgctcag | 120 |
| gtgctttctc cccaacttca cattatttca gtcctcattc atggttaaca tctgcccata | 180 |
| tctcaaggta gggctaaaat aacactttgc tataagacc tgcaatgtag ggaacaaata | 240 |
| gcgcatgctt cacattccac tggccttaat acttccaagc tctctgctcc tgtctggtct | 300 |
| gtgctcactt gtcatacgca gatttaatc catttctctg ccttttccag gtaatctgtc | 360 |

```
acttgtgggt tgccatgcct ggagcataca cagacataac acagagataa cataataggc      420
tcttgttacc agtgaactgg aaagccatgg tccttagcaa aaagactaca gtcagagcac      480
ttttccagac aaagaacaca cgttgtcctg aggagaagtt aatcaagctt tactgaaatg      540
aaagcaaggc agttaagaac agaccttaca acagtcattg cgggctgagt gggaaaccct      600
ggctgactct caagtctttg ctgcgtttac tttccattgt gggttcaggg gacttaggct      660
ttaggggcaa acgtcagccc taggtgtaaa ccagcctctc tgtttaataa atgaaccact      720
gctggagggg gaagtctaat gccagggtca cagggaacgt ggggtgaaga cgtcatggaa      780
gcattgttct agccacacag tctagtatac tgtttcatac cctggtaaat gttaggttta      840
ttttctctta agaatgatgt aatatacact gtagaatgta aacaagatag caagatgact      900
cagtaggtaa cagtccttgc tgcccagttc catggcctaa gtttgttcct agatccccaa      960
gtggtgaaag gagagcagca actctcacaa tttgttcttt gacctccaca catgtaccat     1020
ggcatgtgta tgagcataca ctcactcaca cacacacaca cacattcaca cacagacaca     1080
cacacatagt aaatgtaaaa aaaataagag taatacattg cacataattt atagcaaata     1140
ttttaatatt aggaagcatc tgaaatgtgt aaaatattga gataattgat tgtgataaat     1200
tatatcagtg aagcaacaga ccttgatatt ttcattggta aggtctacta gtgtgtaaca     1260
tttttgacag caagactatc catatttgag atattttgag cctgaatatt ttaatgaaat     1320
ggagtttgat gggagtgttt aaacttcact tgttccsctg ttttggttta gaaaaaaaat     1380
ataattttgt tatatagaaa attcacaaat ggtgttctca ttaaacttta ttttaaagaa     1440
catacctaag acatctatgt gaagtctgta gatgaggctg ttgttgtaaa tttgactatc     1500

<210> SEQ ID NO 8
<211> LENGTH: 1500
<212> TYPE: DNA
<213> ORGANISM: Mus musculus

<400> SEQUENCE: 8
acatcaatcc tagccctggc ccaaatactt ttactggttt aaattttatc cagttttttct     60 ctgtgtgata atatgtattt taatttccat atacttgtat gaaatgaatg taaaactagt      120
gtgcttgcta ttgtgtgaca ttactaatct atgctgttta taatgtgtag tctattaata      180
aagacagaag ggcaagagga agaggataat gacagaaaaa gctcagtagt cccaagagta      240
tacatgtcag tcattaagaa tgtcagttta tcattgacct tcaattggag aaatggctac      300
tggagatatt gtacatacag agagctggat attagaataa aacaaaacag aagagccact      360
gaaatttcac tgtttccata agatattga ttgtgaaatg acacctttac aattttgaac      420
ctaaaataca ataaaattca gtcttccatg tttttaacta gagatgtttt accattttgt      480
ctacatttat gttttccaga aaccatatat gaggaataca tccatctcgt gctacttgtg      540
tttccttcta aacagtcact ttttaactga ggctggcatt catgtcttca ttttggggta      600
atttcatctt tggtcatagc tattatcaag ttagtggcca caatcatttg ttcctgagta      660
tcttgatgtt gaaactgtat tatgttcagt ttccttgtat ataggtcttc actcttcagc      720
gtaggatatc aggtgactgt ggagctgctt gggggacgtg cgaatcctta actgaggatt      780
tcggcacctt ggcagtattc catatgagta ttctatccct taaagcagtt gagcttttg      840 ctataactgt tccatatact gatatcatgt atgtaagttg tcctcattag acagattgtc      900
attggctgac atggtttgtt cctggtcttt tttagaataa ctgttttcc tggggcttta      960 agaatcactc cacagtcacg tgatcagtgt gtcttttatt cgggatatta aatgtgagtt     1020
```

```
ttaaccaaag tgaataaact tgtaatcacc catattgtat ttagcgaaat cttcagtgac    1080
tatgaaatca tcctagcatc agattactgt gggcatcatg aaaagggaca tttactctca    1140
cagttgttaa aggaagtgt taagtgttca aaatcttaca cttactagcc ctaaaagttt    1200
cacggagcct gtacttctag acaactaata atcacttcag aaacattcat taagctatgg    1260
cacagatcag gtgctatctc aatatcatcg tgataaacag attatgtaat aatctgaagc    1320
aggccatctc aggaagatca cctgctaatt attagcttgt cccattataa ctccagacgt    1380
ctgtggttac ttataagcta tccatttagc ctttctctga tcactaagtt ggacagttgg    1440
acagtcttcc tcaaattagc ttagactatc aaaattatac tgtattttg gtatttccat    1500
```

<210> SEQ ID NO 9
<211> LENGTH: 2335
<212> TYPE: DNA
<213> ORGANISM: Artificial Sequence
<220> FEATURE:
<223> OTHER INFORMATION: A fragment

<400> SEQUENCE: 9

```
agttggtggt tatgtgaatc tttgtatttg attgctctta ttcaaattga gatggccctg      60
aaacctgtca gatctgggac actgtgtgaa ataatggctt tgttcttta ttcagacaaa     120 cctggtttta gtctgggcag tcatgggatt tctatgacgc cagatcagat tttctaaatg     180
atgctctcag gagggctaaa tctgatgcat gtgttaagga acacagagcc taccctatgg     240
aaagcagatg tggcataagc accaggcgtt tctctatctg cttctggctt actcgcttgt     300
gttttgatag tcatccttca tcctggttct gttgcaggaa gagttctgga tggatggcag     360
ctggaagccc atcgccatag ccagctcatc ttcaacattg aagctcttac ctgggcatta     420
agtaatgaga atttcgaaac cacatttgag aagtatttcc atccagtgct acttgtgttt     480
acttctaaac agtcattttc taactgaagc tggcattcat gtcttcattt gggctgttt     540 cagtgcaggg cttcctaaaa cagaagccaa ctgggtgaat gtaataagtg atttgaaaaa     600
aattgaagat cttattcaat ctatgcatat tgatgctact ttatatacgg aaagtgatgt     660
tcaccccagt tgcaaagtaa cagcaatgaa gtgctttctc ttggagttac aagttatttc     720
acttgagtcc ggagatgcaa gtattcatga tacagtagaa aatctgatca tcctagcaaa     780
caacagtttg tcttctaatg ggaatgtaac agaatctgga tgcaaagaat gtgaggaact     840
ggaggaaaaa aatattaaag aattttgca gagttttgta catattgtcc aaatgttcat     900
caacacttct tgaaatcaac ctctggatta caaaattgt gaaagattga ctggtattct     960
taactatgtt gctccttta cgctatgtgg atacgctgct ttaatgcctt tgtatcatgc    1020
tattgcttcc cgtatggctt tcatttctc ctccttgtat aaatcctggt tgctgtctct    1080
ttatgaggag ttgtggcccg ttgtcaggca acgtggcgtg gtgtgcactg tgtttgctga    1140
cgcaaccccc actggttggg gcattgccac cacctgtcag ctcctttccg ggactttcgc    1200
tttccccctc cctattgcca cggcggaact catcgccgcc tgccttgccc gctgctggac    1260
aggggctcgg ctgttgggca ctgacaattc cgtggtgttg tcggggaaat catcgtcctt    1320
tccttggctg ctcgcctgtg ttgccacctg gattctgcgc gggacgtcct tctgctacgt    1380
cccttcggcc ctcaatccag cggaccttcc ttcccgcggc ctgctgccgg ctctgcggcc    1440
tcttccgcgt cttcgccttc gccctcagac gagtcggatc tccctttggg ccgcctcccc    1500
gcatcgatac cgtcgacctc gactgtgcct tctagttgcc agccatctgt tgtttgcccc    1560
```

```
tcccccgtgc cttccttgac cctggaaggt gccactccca ctgtcctttc ctaataaaat    1620
gaggaaattg catcgcattg tctgagtagg tgtcattcta ttctgggggg tggggtgggg    1680
caggacagca aggggagga ttgggaagac aatagcaggc atgctgggga aaatagcata     1740
tggcttttct tataaggtca ccttaatctc agttctactt tataataagt cgcatgatta    1800
ctctctaaac atctctggct gcgacagata tgtttctcca agatttatct tgattttaaa    1860
aataagtagc atgggctttg gaaaacaaga ctagcagtat gcctgtattc tttgtgccat    1920
tgttaaggtg ttattacact tcactcagtc tcttttgttc tctaaatgtc tattcacttc    1980
gcacattgtg tctctgaggg caaggtctgg tgctaggcat ctttcagcag agtctacaca    2040
gagtacagac ttctggtgtt taaggtgttg actgacgctg ctctctgtaa ctataaaatc    2100
tctgacagca ctgacaagtc aggtcagaga attaaaactg tgtctatctc agacaaataa    2160
ggtcctaaat aaccaaatta agttttcatg taggagctgt tagaatgaaa aaggatatac    2220 ttcttttga cacaggattt cataactatg tagcgttggg tggcctggaa ctcaccaggg     2280
tagtcctgag cttacagaat cccttgttcc tgtctctctc atcctaggtc cgacg         2335
```

<210> SEQ ID NO 10
<211> LENGTH: 23
<212> TYPE: DNA
<213> ORGANISM: Mus musculus

<400> SEQUENCE: 10
ttgtaaattt gactatcagt tgg                                             23

<210> SEQ ID NO 11
<211> LENGTH: 23
<212> TYPE: DNA
<213> ORGANISM: Mus musculus

<400> SEQUENCE: 11
acagtcattg cgggctgagt ggg                                             23

<210> SEQ ID NO 12
<211> LENGTH: 23
<212> TYPE: DNA
<213> ORGANISM: Mus musculus

<400> SEQUENCE: 12
gagaggctgg tttacaccta ggg                                             23

<210> SEQ ID NO 13
<211> LENGTH: 23
<212> TYPE: DNA
<213> ORGANISM: Mus musculus

<400> SEQUENCE: 13
ctagatcccc aagtggtgaa agg                                             23

<210> SEQ ID NO 14
<211> LENGTH: 23
<212> TYPE: DNA
<213> ORGANISM: Mus musculus

<400> SEQUENCE: 14
taaatttgac tatcagttgg tgg                                             23

<210> SEQ ID NO 15
<211> LENGTH: 23

<212> TYPE: DNA
<213> ORGANISM: Mus musculus

<400> SEQUENCE: 15
gttcagggga cttaggcttt agg        23

<210> SEQ ID NO 16
<211> LENGTH: 23
<212> TYPE: DNA
<213> ORGANISM: Mus musculus

<400> SEQUENCE: 16
taagtcccct gaacccacaa tgg        23

<210> SEQ ID NO 17
<211> LENGTH: 18
<212> TYPE: DNA
<213> ORGANISM: Mus musculus

<400> SEQUENCE: 17
cgttccctgt gaccctgg        18

<210> SEQ ID NO 18
<211> LENGTH: 23
<212> TYPE: DNA
<213> ORGANISM: Mus musculus

<400> SEQUENCE: 18
ttcataccct ggtaaatgtt agg        23

<210> SEQ ID NO 19
<211> LENGTH: 23
<212> TYPE: DNA
<213> ORGANISM: Mus musculus

<400> SEQUENCE: 19
acaaacttag gccatggaac tgg        23

<210> SEQ ID NO 20
<211> LENGTH: 23
<212> TYPE: DNA
<213> ORGANISM: Mus musculus

<400> SEQUENCE: 20
ggattgatgt cgtcggacct agg        23

<210> SEQ ID NO 21
<211> LENGTH: 23
<212> TYPE: DNA
<213> ORGANISM: Mus musculus

<400> SEQUENCE: 21
agggctagga ttgatgtcgt cgg        23

<210> SEQ ID NO 22
<211> LENGTH: 23
<212> TYPE: DNA
<213> ORGANISM: Mus musculus

<400> SEQUENCE: 22
cataactatg tagcgttggg tgg        23

<210> SEQ ID NO 23
<211> LENGTH: 23
<212> TYPE: DNA
<213> ORGANISM: Mus musculus

<400> SEQUENCE: 23
atttcataac tatgtagcgt tgg					23

<210> SEQ ID NO 24
<211> LENGTH: 23
<212> TYPE: DNA
<213> ORGANISM: Mus musculus

<400> SEQUENCE: 24
gacgacatca atcctagccc tgg					23

<210> SEQ ID NO 25
<211> LENGTH: 23
<212> TYPE: DNA
<213> ORGANISM: Mus musculus

<400> SEQUENCE: 25
aaagtatttg ggccagggct agg					23

<210> SEQ ID NO 26
<211> LENGTH: 23
<212> TYPE: DNA
<213> ORGANISM: Mus musculus

<400> SEQUENCE: 26
ttcgcacatt gtgtctctga ggg					23

<210> SEQ ID NO 27
<211> LENGTH: 23
<212> TYPE: DNA
<213> ORGANISM: Mus musculus

<400> SEQUENCE: 27
ctacacagag tacagacttc tgg					23

<210> SEQ ID NO 28
<211> LENGTH: 23
<212> TYPE: DNA
<213> ORGANISM: Mus musculus

<400> SEQUENCE: 28
attttaaaaa taagtagcat ggg					23

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
ttgtaaattt gactatcagt					20

<210> SEQ ID NO 30
<211> LENGTH: 24
<212> TYPE: DNA
<213> ORGANISM: Artificial Sequence
<220> FEATURE:

<223> OTHER INFORMATION: Synthetic primer

<400> SEQUENCE: 30
taggttgtaa atttgactat cagt                                      24

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
actgatagtc aaatttacaa                                           20

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
aaacactgat agtcaaattt acaa                                      24

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
agggctagga ttgatgtcgt                                           20

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
taggagggct aggattgatg tcgt                                      24

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
acgacatcaa tcctagccct                                           20

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
aaacgacatc aatcctagcc ct                                        22

```
<210> SEQ ID NO 37
<211> LENGTH: 132
<212> TYPE: DNA
<213> ORGANISM: Artificial Sequence
<220> FEATURE:
<223> OTHER INFORMATION: T7 promoter and sgRNA scaffold

<400> SEQUENCE: 37
gaattctaat acgactcact atagggggtc ttcgagaaga cctgttttag agctagaaat      60
agcaagttaa ataaggcta gtccgttatc aacttgaaaa agtggcaccg agtcggtgct     120
tttaaaggat cc                                                        132

<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
gggcaccagc cacctatttt gatga                                           25

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
atccaggtgg caacacaggc                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
tgcactgtgt ttgctgacgc                                                 20

<210> SEQ ID NO 41
<211> LENGTH: 25
<212> TYPE: DNA
<213> ORGANISM: Artificial Sequence
<220> FEATURE:
<223> OTHER INFORMATION: Synthetic primer

<400> SEQUENCE: 41
aaaccaagct ctttggagga gggtg                                           25

<210> SEQ ID NO 42
<211> LENGTH: 25
<212> TYPE: DNA
<213> ORGANISM: Artificial Sequence
<220> FEATURE:
<223> OTHER INFORMATION: Synthetic primer

<400> SEQUENCE: 42
ttgccctcca gtggctcact atttc                                           25

<210> SEQ ID NO 43
<211> LENGTH: 25
<212> TYPE: DNA
```

```
<213> ORGANISM: Artificial Sequence
<220> FEATURE:
<223> OTHER INFORMATION: Synthetic primer

<400> SEQUENCE: 43
acatattgag agaccgcctg accct                                          25

<210> SEQ ID NO 44
<211> LENGTH: 22
<212> TYPE: DNA
<213> ORGANISM: Artificial Sequence
<220> FEATURE:
<223> OTHER INFORMATION: Synthetic primer

<400> SEQUENCE: 44
gtggatacgc tgctttaatg cc                                             22

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
aagggagatc cgactcgtct                                                20

<210> SEQ ID NO 46
<211> LENGTH: 50
<212> TYPE: DNA
<213> ORGANISM: Artificial Sequence
<220> FEATURE:
<223> OTHER INFORMATION: Synthetic primer

<400> SEQUENCE: 46
gctatgcatc aagcttggta ccgataccag tgaactggaa agccatggtc                50

<210> SEQ ID NO 47
<211> LENGTH: 49
<212> TYPE: DNA
<213> ORGANISM: Artificial Sequence
<220> FEATURE:
<223> OTHER INFORMATION: Synthetic primer

<400> SEQUENCE: 47
aataacttaa tcgtggagga tgatcctctt cctcttgccc ttctgtctt                 49

<210> SEQ ID NO 48
<211> LENGTH: 432
<212> TYPE: DNA
<213> ORGANISM: Homo sapiens

<400> SEQUENCE: 48
tggctgcaga gcctgctgct cttgggcact gtggcctgca gcatctctgc acccgcccgc     60
tcgcccagcc ccagcacgca gccctgggag catgtgaatg ccatccagga ggcccggcgt    120
ctcctgaacc tgagtagaga cactgctgct gagatgaatg aaacagtaga agtcatctca    180
gaaatgtttg acctccagga gccgacctgc tacagaccc gcctggagct gtacaagcag    240
ggcctgcggg gcagcctcac caagctcaag ggccccttga ccatgatggc cagccactac    300
aagcagcact gccctccaac cccggaaact tcctgtgcaa cccagattat cacctttgaa    360
agtttcaaag agaacctgaa ggactttctg cttgtcatcc cctttgactg ctgggagcca    420
gtccaggagt ga                                                       432
```

<210> SEQ ID NO 49
<211> LENGTH: 1665
<212> TYPE: DNA
<213> ORGANISM: Homo sapiens

<400> SEQUENCE: 49

| | |
|---|---|
| atgaccgcgc cgggcgccgc cgggcgctgc cctcccacga catggctggg ctccctgctg | 60 |
| ttgttggtct gtctcctggc gagcaggagt atcaccgagg aggtgtcgga gtactgtagc | 120 |
| cacatgattg ggagtggaca cctgcagtct ctgcagcggc tgattgacag tcagatggag | 180 |
| acctcgtgcc aaattacatt tgagtttgta gaccaggaac agttgaaaga tccagtgtgc | 240 |
| taccttaaga aggcatttct cctggtacaa gacataatgg aggacaccat gcgcttcaga | 300 |
| gataacaccc ccaatgccat cgccattgtg cagctgcagg aactctcttt gaggctgaag | 360 |
| agctgcttca ccaaggatta tgaagagcat gacaaggcct gcgtccgaac tttctatgag | 420 |
| acacctctcc agttgctgga aaggtcaag aatgtcttta tgaaacaaa gaatctcctt | 480 |
| gacaaggact ggaatatttt cagcaagaac tgcaacaaca gctttgctga atgctccagc | 540 |
| caagatgtgg tgaccaagcc tgattgcaac tgcctgtacc ccaaagccat ccctagcagt | 600 |
| gacccggcct ctgtctcccc tcatcagccc ctcgcccct ccatggcccc tgtggctggc | 660 |
| ttgacctggg aggactctga gggaactgag ggcagctccc tcttgcctgg tgagcagccc | 720 |
| ctgcacacag tggatccagg cagtgccaag cagcggccac ccaggagcac tgccagagc | 780 |
| tttgagccgc cagagacccc agttgtcaag gacagcacca cggtggctc accacagcct | 840 |
| cgcccctctg tcggggcctt caaccccggg atggaggata ttcttgactc tgcaatgggc | 900 |
| actaattggg tcccagaaga agcctctgga gaggccagtg agattcccgt accccaaggg | 960 |
| acagagcttt ccccctccag gccaggaggg ggcagcatgc agacagagcc cgccagaccc | 1020 |
| agcaacttcc tctcagcatc ttctccactc cctgcatcag caagggcca acagccggca | 1080 |
| gatgtaactg gtaccgcctt gcccagggtg ggccccgtga ggcccactgg ccaggactgg | 1140 |
| aatcacaccc cccagaagac agaccatcca tctgccctgc tcagagaccc cccggagcca | 1200 |
| ggctctccca ggatctcatc actgcgcccc cagggcctg gcaaccctc caccctctct | 1260 |
| gctcagccac agcttttccag aagccactcc tcgggcagcg tgctgcccct tggggagctg | 1320 |
| gagggcagga ggagcaccag ggatcggagg agccccgcag agccagaagg aggaccagca | 1380 |
| agtgaagggg cagccaggcc cctgccccgt tttaactccg ttcctttgac tgacacaggc | 1440 |
| catgagaggc agtccgaggg atccttcagc ccgcagctcc aggagtctgt cttccacctg | 1500 |
| ctggtgccca gtgtcatcct ggtcttgctg gccgtcggag gcctcttgtt ctacaggtgg | 1560 |
| aggcggcgga gccatcaaga gcctcagaga gcggattctc ccttggagca accagagggc | 1620 |
| agcccctga ctcaggatga cagacaggtg gaactgccag tgtag | 1665 |

<210> SEQ ID NO 50
<211> LENGTH: 455
<212> TYPE: DNA
<213> ORGANISM: Homo sapiens

<400> SEQUENCE: 50

| | |
|---|---|
| agccgcctgc ccgtcctgct cctgctccaa ctcctggtcc gccccggact ccaagctccc | 60 |
| atgacccaga caacgcccct gaagacaagc tgggttaact gctctaacat gatcgatgaa | 120 |
| attataacac acttaaagca gccacctttg cctttgctgg acttcaacaa cctcaatggg | 180 |

```
gaagaccaag acattctgat ggaaaataac cttcgaaggc caaacctgga ggcattcaac      240
agggctgtca agagtttaca gaacgcatca gcaattgaga gcattcttaa aaatctcctg      300
ccatgtctgc ccctggccac ggccgcaccc acgcgacatc caatccatat caaggacggt      360
gactggaatg aattccggag gaaactgacg ttctatctga aaaccttga gaatgcgcag       420 gctcaacaga cgactttgag cctcgcgatc ttttg                                 455

<210> SEQ ID NO 51
<211> LENGTH: 489
<212> TYPE: DNA
<213> ORGANISM: Artificial Sequence
<220> FEATURE:
<223> OTHER INFORMATION: Humanized IL 15

<400> SEQUENCE: 51
atgagaattt cgaaaccaca tttgagaagt atttccatcc agtgctactt gtgtttactt       60
ctaaacagtc attttctaac tgaagctggc attcatgtct tcattttggg ctgtttcagt      120 gcaggcttc ctaaaacaga agccaactgg gtgaatgtaa taagtgattt gaaaaaaatt      180
gaagatctta ttcaatctat gcatattgat gctactttat atacggaaag tgatgttcac      240
cccagttgca aagtaacagc aatgaagtgc tttctcttgg agttacaagt tatttcactt      300
gagtccggag atgcaagtat tcatgataca gtagaaaatc tgatcatcct agcaaacaac      360
agtttgtctt ctaatgggaa tgtaacagaa tctggatgca aagaatgtga ggaactggag      420
gaaaaaaata ttaaagaatt tttgcagagt tttgtacata ttgtccaaat gttcatcaac      480
acttcttga                                                              489
```